United States Patent
Vasiljeva et al.

(10) Patent No.: US 9,827,337 B2
(45) Date of Patent: Nov. 28, 2017

(54) CATHEPSIN-BINDING COMPOUNDS BOUND TO A CARRIER AND THEIR DIAGNOSTIC USE

(75) Inventors: Olga Vasiljeva, Domzale (SI); Georgy Mikhaylov, Almaty (KZ); Boris Turk, Skofljica (SI); Norbert Schaschke, Bielefeld (DE)

(73) Assignee: J. Stefan Institute, Ljubljana (SI)

( * ) Notice: Subject to any disclaimer, the term of this patent is extended or adjusted under 35 U.S.C. 154(b) by 422 days.

(21) Appl. No.: 14/127,758

(22) PCT Filed: Jun. 22, 2012

(86) PCT No.: PCT/EP2012/002652
§ 371 (c)(1),
(2), (4) Date: Mar. 25, 2014

(87) PCT Pub. No.: WO2012/175223
PCT Pub. Date: Dec. 27, 2012

(65) Prior Publication Data
US 2014/0227175 A1 Aug. 14, 2014

(30) Foreign Application Priority Data
Jun. 22, 2011 (EP) .................................. 11005110

(51) Int. Cl.
| | | |
|---|---|---|
| *A61K 51/00* | (2006.01) | |
| *A61M 36/14* | (2006.01) | |
| *A61K 51/08* | (2006.01) | |
| *A61K 47/48* | (2006.01) | |
| *A61K 49/00* | (2006.01) | |
| *A61K 49/18* | (2006.01) | |
| *A61K 31/00* | (2006.01) | |
| *A61K 9/127* | (2006.01) | |
| *A61K 38/08* | (2006.01) | |
| *A61K 49/08* | (2006.01) | |

(52) U.S. Cl.
CPC ............. *A61K 51/08* (2013.01); *A61K 9/127* (2013.01); *A61K 31/00* (2013.01); *A61K 38/08* (2013.01); *A61K 47/48815* (2013.01); *A61K 49/0002* (2013.01); *A61K 49/005* (2013.01); *A61K 49/0052* (2013.01); *A61K 49/0063* (2013.01); *A61K 49/085* (2013.01); *A61K 49/1812* (2013.01)

(58) Field of Classification Search
CPC ........ A61K 49/00; A61K 47/00; A61K 38/00; A61K 51/00; A61K 9/127; A61K 47/48815; A61K 49/0002; A61K 49/0052; A61K 49/0063; A61K 49/1812; A61K 31/00; A61K 38/08; A61K 49/005; A61K 49/085; A61K 51/08; A61K 9/00
USPC .......... 424/1.11, 1.49, 1.65, 1.69, 1.73, 1.81, 424/1.85, 1.89, 9.1, 9.2, 9.3, 9.4, 9.5, 9.6, 424/1.29, 400, 450; 514/1, 1.1, 19.2, 514/19.3, 19.4, 19.5, 19.6, 20.1, 21.2, 514/21.3, 21.4, 21.5, 21.6, 21.7, 21.8, 514/21.9, 21.91
See application file for complete search history.

(56) References Cited

U.S. PATENT DOCUMENTS

| | | | | |
|---|---|---|---|---|
| 6,143,716 A | * | 11/2000 | Meers ..................... | A61K 9/127 424/450 |
| 7,687,524 B2 | * | 3/2010 | Boyd .................... | A61K 31/277 514/357 |
| 2003/0036102 A1 | * | 2/2003 | Bandman ............... | C07K 16/40 435/7.23 |
| 2005/0002865 A1 | | 1/2005 | Klaveness et al. | |

FOREIGN PATENT DOCUMENTS

| | | | |
|---|---|---|---|
| WO | WO 02/096367 | * | 12/2002 |
| WO | WO-02/096367 A2 | | 12/2002 |

OTHER PUBLICATIONS

Cegnar et al., "Poly(lactide-co-glycolide) nanoparticles as a carrier system for delivering cysteine protease inhibitor cystatin into tumor cells," Exp Cell Res 301(2): 223-31 (2004).
Greenbaum et al., "Epoxide electrophiles as activity-dependent cysteine protease profiling and discovery tools," Chem Biol. 7(8): 569-81 (2000).
Jaffer et al., "Optical and multimodality molecular imaging: insights into atherosclerosis," Arterioscler Thromb Vasc Biol. 29(7): 1017-24 (2009).
Mikhaylov et al, "Ferri-liposomes as an MRI-visible drug-delivery system for targeting tumours and their microenvironment," Nat Nanotechnol. 6(9): 594-602 (2011).
Schaschke et al., "Beta-cyclodextrin/epoxysuccinyl peptide conjugates: a new drug targeting system for tumor cells," Biorg Med Chem Lett. 10(7): 677-80 (2000).
Schaschke et al., "Epoxysuccinyl peptide-derived affinity labels for cathepsin B," FEBS Lett. 482(1-2): 91-96 (2000).
International Preliminary Report on Patentability and Written Opinion issued for PCT/EP2012/002652 dated Dec. 23, 2013.

\* cited by examiner

*Primary Examiner* — D L Jones
(74) *Attorney, Agent, or Firm* — Clark & Elbing LLP

(57) ABSTRACT

The invention relates to Cathepsin-binding compounds bound to a carrier comprising a diagnostic moiety, for use in the diagnosis of inflammatory diseases, and/or for use in the diagnosis of neoplastic diseases, wherein the Cathepsin-binding compound binds to inflammatory cells of the tumour stroma. The invention also relates to Cathepsin B-targeting compounds and Cathepsin B-binding and liposome-binding compounds.

3 Claims, 6 Drawing Sheets

A

B

C

CATHEPSIN-BINDING COMPOUNDS BOUND TO A CARRIER AND THEIR DIAGNOSTIC USE

CROSS-REFERENCE TO RELATED APPLICATIONS

Figure 1:
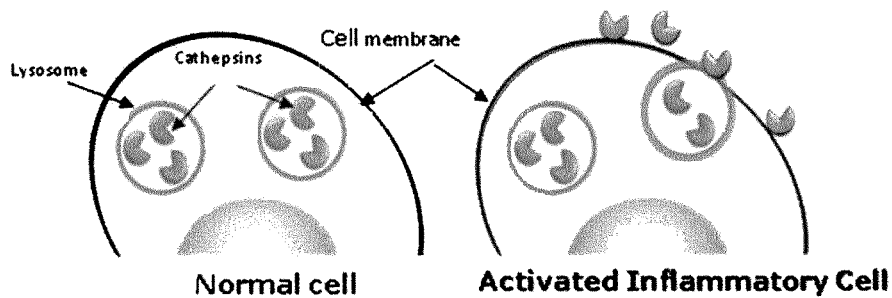
Figure 1:
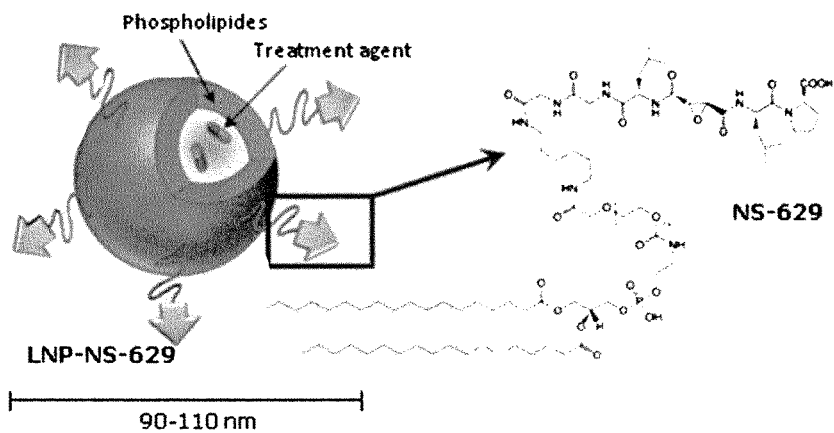
Figure 1:
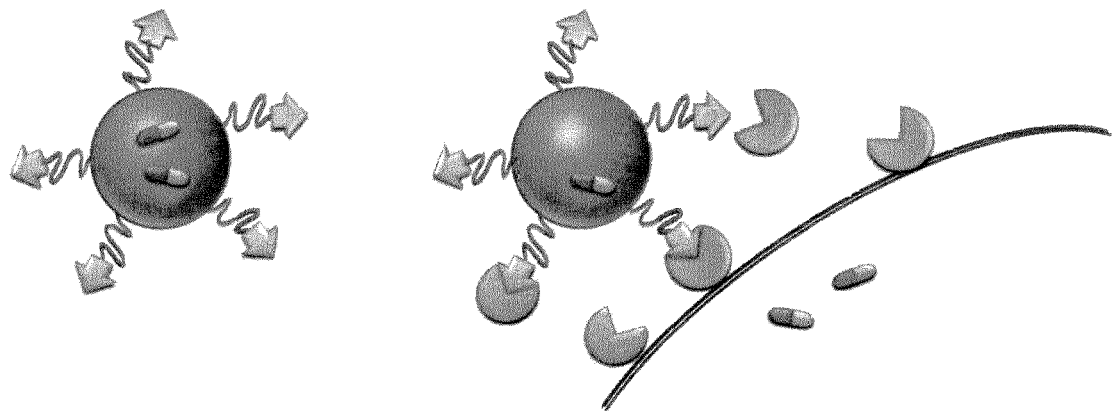

This application is a national phase of International Application No. PCT/EP2012/002652, filed Jun. 22, 2012, which claims priority from European Application No. EP11005110.9, filed Jun. 22, 2011, both hereby incorporated by reference.

The invention relates to Cathepsin-binding compounds bound to a carrier comprising a therapeutic and/or diagnostic moiety, for use in the diagnosis and/or treatment of inflammatory diseases, and/or for use in the diagnosis and/or treatment of neoplastic diseases, wherein the Cathepsin-binding compound binds to inflammatory cells of the tumour stroma. The invention also relates to Cathepsin B-targeting compounds and Cathepsin B-binding and liposome-binding compounds.

BACKGROUND

Inflammation is an essential localized host response to invading microorganisms or tissue injury which involves cells of the immune system. The classic signs of inflammation include redness (erythema), swelling (edema), pain and increased heat production (pyrema) at the site of injury. The inflammatory response allows the body to specifically recognize and eliminate an invading organism and/or repair tissue injury. Inflammatory disease occurs when an inflammatory response is initiated that is inappropriate and/or does not resolve in the normal manner but rather persists and results in a chronic inflammatory state. Inflammatory disease may be systemic (e.g. lupus) or localized to particular tissues or organs and exerts an enormous personal and economic burden to the society. Examples of some of the most common and problematic inflammatory diseases are rheumatoid arthritis, inflammatory bowel disease, psoriasis, asthma, chronic obstructive pulmonary disease, emphysema, colitis and ischemia-reperfusion injury.

Proteases, and particularly lysosomal cysteine proteases, have recently been considered as pharmacological targets for immune disorders and inflammatory diseases, including rheumatoid arthritis, atherosclerosis, and myasthenia gravis (Link et al., 2006; Riese, R. J. et al., Immunity 1996, 4, 357; Thurmond et al. (1), 2004; Vasiljeva et al., 2007). An inflammatory cell infiltrate is an important component of the tumour microenvironment, and many clinical studies have established a positive correlation between inflammation and tumour progression (Mantovani et al., 2008). Also, stromal cells that infiltrate the tumour mass can secrete a variety of tumour-promoting factors including growth factors, chemokines, and proteases (Murdoch et al., 2008).

Proteases can be very harmful if not strictly controlled. There is a growing body of information that cysteine cathepsins are involved in numerous pathologies, with at least some of them representing suitable targets for therapy. One of the areas, where cysteine cathepsins have gathered a lot of attraction recently is cancer biology, especially after the failure of the MMP inhibitors in clinical trials (Coussens et al., 2002; Turk et al., 2004). The other emerging areas include viral infections, cardiovascular diseases and osteoarthritis, although the major focus is still on osteoporosis, rheumatoid arthritis and other diseases linked with the immune system.

There is increasing evidence that cysteine proteases, mostly cathepsins B and L, and to a lesser extend cathepsins H, S, X, and K, contribute to the proteolytic events during tumour progression. Cysteine cathepsins upregulation has been reported for many human tumours, including breast, lung, brain, gastrointestinal, prostate cancer, and melanoma (Jedesko et al., 2004). The expression of lysosomal proteases, e.g. cathepsins B and L, have often been positively correlated with a poor prognosis for patients with a variety of malignancies, and antigen levels of cysteine cathepsins were measured as potential prognostic markers for several types of cancer.

Cysteine proteases have been implicated in the progression of tumours from a premalignant to a malignant state and in various critical tumourbiological processes, including tumour cell hyperproliferation and apoptosis; tumour induced angiogenesis, as well as invasion of surrounding tissues and metastasis by malignant cells, suggesting that they are relevant drug targets for treating cancer (Turk et al., 2004).

Rheumatoid arthritis is a chronic inflammatory joint disorder involving autoimmune processes that result in destruction of joint cartilage eventually leading to loss of joint function. In RA, the synovial membrane proliferates to form a pannus that destroys adjacent bone and cartilage. Among the cells mainly responsible for cartilage damage are fibroblast-like synoviocytes (synovial fibroblasts) and activated macrophages that accumulate in the interface between pannus and cartilage.

Cathepsin B and, to a lesser extent, cathepsin L were found in the synovial fluids (Turk et al., 1988; Huet et al., 1993) and synovial lining tissues of patients with rheumatoid arthritis (Esser at al., 1994). Both enzymes have been detected at high levels in membranes of patients with rheumatoid arthritis, even at very early stages, while their levels were very low in normal synovium (Hansen et al., 2000). Keyszer and co-authors proposedpost-transcriptional up-regulation of these enzymes in rheumatoid arthritis (Keyszer et al., 1998). In addition, selective secretion of cathepsins B and L by synovial fibroblast-like cells upon cytokine induction was observed (Lemaire et al., 1997). In experimental animal models increased levels of cathepsin B have been detected in joint tissues during the course of experimental arthritis (Esser et al., 1994; Etherington et al., 1988), while elevated levels of cathepsin L have been detected in the synovial lining of rabbits with antigen-induced arthritis (Etherington et al., 1988). Furthermore, involvement of cathepsins B and L in bone degradation was demonstrated by inhibition of bone resorption by selective inactivators of cysteine proteases (Hill et al., 1994). Using retroviral gene transfer, ribozymes cathepsin L mRNA, specifically inhibiting the synthesis of cathepsin L, reduced cartilage destruction in vitro and in vivo using a mouse co-implantation model of rheumatoid arthritis (Schedel et al., 2004).

Innate immune cells can constitute a substantial proportion of the cells within the tumour microenvironment and have been associated with tumour malignancy in patients and animal models of cancer (Mantovani et al., 2008; Murdoch et al., 2008); however, the mechanisms by which they modulate tumour progression are incompletely understood. It was shown that high levels of Cathepsin protease activity are induced in the majority of macrophages in the microenvironment of pancreatic islet cancers, mammary tumours, and lung metastases during malignant progression (Gocheva et al., 2010). It was also shown that tumour-associated macrophage (TAM)-supplied Cathepsins B and S are critical for promoting pancreatic tumour growth, angiogenesis, and invasion in vivo, and markedly enhance the invasiveness of cancer cells in culture. It was demonstrated that interleukin-4 (IL-4) is responsible for inducing Cathepsin activity in macrophages in vitro and in vivo, hence being an important regulator, and Cathepsin proteases as critical mediators, of the tumour-promoting functions of TAMs (Gocheva et al., 2010).

There are 11 human cysteine Cathepsin proteases (Cts) (B, C, H, F, K, L, O, S, V, W, and X/Z), that share a conserved active site formed by cysteine and histidine residues. Cathepsins not only mediate terminal protein degradation in the lysosomes, but they also process and activate proteins including growth factors, transcription factors, and other proteases (Vasiljeva et al., 2007). For many years cysteine Cathepsins were believed to be localized exclusively in lysosomes, however, during pathological processes Cathepsins are found in other cellular compartments or extracellularly (Jane et al., 2006), and at the plasma membrane (Mohamed and Sloane, 2006; Jane et al., 2006; Lechner et al., 2006). Besides their main function as lysosomal protein recycling machinery, the Cathepsins are known to participate in numerous physiological processes such as activation of proenzymes and prohormones (Friedrichs et al., 2003; Wolters et al., 2001), MHC-II antigen processing and presentation (Honey et al., 2002), bone remodeling (Potts et al., 2004), keratinocyte differentiation (Roth et al., 2000; Reinheckel et al., 2005) and several others (Vasiljeva et al., 2007). However, proteases can be very harmful if not strictly controlled. There is a growing body of information that cysteine Cathepsins are involved in numerous pathologies, like in particular cancer biology, but also viral infections, cardiovascular diseases and osteoarthritis, although the major focus is still on osteoporosis, rheumatoid arthritis, atherosclerosis and other diseases linked with the immune system (reviewed in Vasiljeva et al., 2007).

Interestingly, clinical studies in various tumour types have shown that certain Cathepsins, including Cts B, L, and S, are supplied to the tumour by stromal cells (Iacobuzio-Donahue et al. 1997; Hazen et al. 2000; Lindahl et al. 2009; Sullivan et al. 2009). This interplay between different cell types in the tumour microenvironment is highly complex, and therapeutic implications are thus difficult to predict.

A major role for cysteine Cathepsin proteases, produced by leukocytes and epithelial cells, as important mediators of tumour development, has also been recently appreciated (Turk et al., 2004). While many cysteine Cathepsins are lysosomal proteases, they are known to be involved in remodelling of ECM, to regulate cellular proliferation and death, to activate tumour angiogenesis, to promote invasion and metastasis of tumour cells, and to regulate inflammatory and immune responses in tissues (Chapman et al., 1997). Joyce and colleagues recently demonstrated the association of increased Cathepsin activity with angiogenic vasculature and invasive fronts of carcinomas during tumourigenesis in transgenic mouse models of Islet cell and cervical carcinogenesis using activity-based chemical probes and in vivo imaging (Joyce et al., 2004).

Cathepsins inhibitors were proposed for use in treatment of diseases associated with Cathepsins overexpression and/or secretion such as rheumatoid arthritis, osteoarthritis, atherosclerosis, neoplastic diseases and others. WO 2004/033445 describes compounds which are useful for treating diseases in which Cathepsin-dependent bone resorption was indicated. WO 2004/033445 relates to a method of treating or preventing diseases such as osteoporosis, Paget's disease, periodontal disease, tooth loss, bone fractures, rheumatoid arthritis, osteoarthritis, periprosthetic osteolysis, and some others using 4-amino-azepan-3-one cysteine proteases inhibitor. The use of specific inhibitors of Cathepsins L, B, S for treatment and prevention of diseases and disorders associated with these Cathepsins is described in patent WO 2009/136997.

WO 2009/133545 reports a drug targeting strategy for selective delivery of the anticancer drugs to endothelial cells by polymer-drug conjugates modified with a carbohydrate ligand. The use of such specific ligand is limited to the targeting of endothelial cells only. There is therefore a need for the identification and validation of novel surface antigens expressed on tumour cells.

Cathepsin cleavable peptide linkers are e.g. shown in (Jaffer et al., 2009). Those linkers could be cleaved by cathepsins. The cleavage will be used in that case for "liberating fluorochromes from the backbone and consequently generating strong fluorescence".

The system developed in (Cegnar et al., 2004) was designed to be used for the inhibition of intracellular cathepsins. Cathepsin inhibitor, cystatin C, was "incorporated" as a drug, thus have been used as treatment compound transported being entrapped in the system. Notably, the tumour cell-centered view of the metastatic process has been recently revised and the gained information on crosstalk between tumour cells and its surrounding tissue, or tumour stroma (Liotta and Kohn, 2001), supported the notion that the microenvironment is at least as determinative for tumour progression as the intrinsic features of tumour cells (Mueller and Fusenig, 2004). Thus, Cathepsins have been recently reported to be mainly overexpressed by tumour stromal cells (Vasiljeva et al., 2006; Gocheva et al., 2010). There is a need for novel approaches for the selective treatment of inflammatory and neoplastic diseases, with limited side effects. Therefore, a targeted approach is desirable. Moreover, there is a need for a reliable diagnosis of inflammatory and neoplastic diseases.

Although there are hints for a role of Cathepsins, in particular Cathepsin B, in the development and/or progression of various diseases, abundance of the Cathepsins in the human body and the complexity of the potential role of extracellular or membrane-localized Cathepsins appeared to make this target unsuitable for a targeting approach for delivering diagnostic and/or therapeutic moieties to a disease site. This is in particular true, as extracellularly localized Cathepsin is expected to be insufficiently close to cells to be targeted.

Compounds that will target cathepsins will target the site of disease (e.g. inflammation or neoplastic). Depends on the disease of interest where cathepsins are participated such a targeting system would enable targeted drug delivery to the site of the disease. Cysteine cathepsins are normally intracellular enzymes, thus their appearance extracellular could occur only at the site of the disease, thus enabling the fine targeting of medicine avoiding any possible toxic side effects.

Surprisingly, it could be shown in the Examples, that a Cathepsin-binding compound NS-629 bound to liposomes can surprisingly be used for binding to inflammatory cells. Moreover, it could surprisingly be shown in the Examples, that NS-629 bound to liposomes, wherein the liposomes carry a diagnostic label, like luciferine or the MRI agent Gd-DTPA, respectively, can be used for in vivo diagnosing inflammatory diseases, and/or neoplastic diseases, by binding to cells of the tumour stroma, and that the compound surprisingly targets to the disease site in vivo.

The present invention relates to a Cathepsin-binding compound bound to a carrier comprising a therapeutic and/or diagnostic moiety,
(i) for use in the diagnosis and/or treatment of inflammatory diseases, and/or
(ii) for use in the diagnosis and/or treatment of neoplastic disease, wherein the Cathepsin-binding compound binds to inflammatory cells of the tumour stroma.

A Cathepsin-binding compound bound to a carrier preferably has following structure of formula (V):

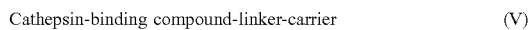

Cathepsin-binding compound-linker-carrier    (V)

It is understood, that in case of covalent linkage of the Cathepsin-binding compound to a linker, a Cathepsin-binding moiety is linked via at least one chemical bond to the linker. For example, MeO-Gly-Gly-Leu-(2S,3S)-tEps-Leu-Pro-OH is described as Cathepsin-binding compound. In NS-629, the Cathepsin-binding moiety of this compound linked to the linker is -Gly-Gly-Leu-(2S,3S)-tEps-Leu-Pro-OH.

In a further embodiment, a Cathepsin-binding compound bound to a carrier has following structure of formula (VI):

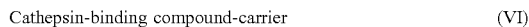

Cathepsin-binding compound-carrier    (VI)

"Cathepsin" (Cts) according to the present invention is understood as a mammalian cysteine protease, in particular a human, rat, monkey, dog, cat, pig, cow or horse Cathepsin protease (Cts), more preferably a human cysteine protease. Preferably, the Cathepsin is Cts B, C, H, F, K, L, O, S, V, W, or X/Z, more preferably the Cathepsin is Cts B, even more preferably human Cts B, most preferably human Cts B having the NCBI Accession number AAC37547.1, AAH95408.1, AAH10240.1, or CAA77178.1.

Thus, in a preferred embodiment, the Cathepsin bound by the compound is selected from Cathepsin (Cts) B, C, H, F, K, L, O, S, V, W, and X/Z. In particular, the Cathepsin bound by the compound is overexpressed in an inflammatory and/or neoplastic disease, more preferably it is excessively located in the extracellular matrix of affected tissue in an inflammatory and/or neoplastic disease. Preferably, the Cathepsin bound by the compound is selected from Cts B, and/or S, more preferably the compound is selected from Cts B.

Thus, in a further preferred embodiment, the Cathepsin is mammalian Cathepsin B, in particular human, rat, monkey, dog, cat, pig, cow or horse Cathepsin B, more preferably human Cathepsin B.

"Cathepsin-binding compound" is understood as compound having a $K_D$ value with respect to at least one Cathepsin of less than about 100 μM, preferably less than about 10 μM, more preferably less than about 1 μM, even more preferably less than about 1 μM, especially preferably less than about 100 nM, most preferably less than about 10 nM, as determined in an assay described in Bieth, 1995, or by surface plasmon resonance described in Mirkovic et al., 2009. In one embodiment, the compound has a $K_D$ value with respect to one Cathepsin of less than about 10 nM, and the $K_D$ value with respect to at least one other Cathepsins is at least 10-fold, more preferably at least 100-fold higher than the $K_D$ value with respect to one Cathepsin. Such compounds bind specifically to one Cathepsin. In a preferred embodiment, the compound binding specifically to one Cathepsin is an antibody or antibody fragment. The Cathepsin-binding compound may be any kind of compound, in particular, it is selected from an antibody or antibody fragment specifically binding to Cathepsin, a synthetic inhibitor of Cathepsin, a peptide, a protein and an antibody mimetic.

In a further embodiment, the Cathepsin-binding compound is a protein or compound specifically binding to Cathepsin. In a preferred embodiment, the compound is a synthetic inhibitor of Cathepsin. In a further preferred embodiment, the compound is an inhibitor of the protease activity of a Cathepsin. The use of an inhibitor of the protease activity of a Cathepsin as a Cathepsin-binding compound enables to combine both the targeted delivery of therapeutically active compounds and the therapeutic effect of Cathepsin protease inhibition itself.

Herein, the term "antibody or antibody fragment" is understood as meaning antibodies, antibody fragments, or antigen-binding parts thereof, in particular complementarity-determining regions (CDRs) of antibodies, which have been prepared recombinantly and, where appropriate, modified, such as chimaeric antibodies, human antibodies, humanized antibodies, multifunctional antibodies, bispecific or oligospecific antibodies, single-chain antibodies and Fab, Fab' or F(ab)$_2$ fragments, or single domain VHH, VH or VL single domains, camelid antibodies and lama antibodies (see for example, Harmsen and De Haard, 2007; Holliger and Hudson, 2005; EP-B1-0 368 684, U.S. Pat. Nos. 4,816,567, 4,816,397, WO 88/01649, WO 93/06213 or WO 98/24884), fragments produced by a Fab expression library, anti-idiotypic (anti-Id) antibodies, and epitope-binding fragments of any of the above. The antibody is preferably a human IgG1 antibody. However, other human antibody isotypes are also encompassed by the invention, including IgG2, IgG3, IgG4, IgM, IgA1, IgA2, IgAsec, IgD and IgE. Also animal-derived antibodies of various isotypes can be used according to the invention.

An "amino-compound" according to the present invention is a compound of the general formula NR$^1$R$^2$R$^3$, wherein R$^1$, R$^2$ and R$^3$ are selected from the group consisting of H, aliphatic and aromatic organic substituents.

"Antibody mimetics" according to the present invention are protein scaffolds different from antibodies and antibody fragments, e.g. DARPINs or anticalins which are based on lipocalin (Beste et al., 1999). The natural ligand-binding sites of the lipocalins, for example the retinol-binding protein or the bilin-binding protein, can be altered, for example by means of a "combinatorial protein design" approach, in such a way that they bind to selected haptens (Skerra (1), 2000). Other known protein scaffolds are known as being alternatives to antibodies for molecular recognition (Skerra (2), 2000). Designed ankyrin repeat proteins (DARPins) are a promising class of non-immunoglobulin proteins that can offer advantages over antibodies for target binding in drug discovery and drug development. DARPins specifically targeting the tumour marker HER2 have also been generated and were shown to function in both in vitro diagnostics and in vivo tumour targeting. DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple receptors with one molecule composed of several DARPins.

"About" according to the present invention is understood as meaning the experimental error range, in particular ±5% or ±10%.

An "inhibitor of the protease activity of a Cathepsin" is understood as compound having a second order rate constant with respect to at least one Cathepsin of at least about $10^3$, preferably at least about $10^4$, more preferably at least about $10^5$, even more preferably at least about $10^6$ $k_2/k_1$ ($M^{-1}$ $s^{-1}$) as determined in an assay described in Schaschke et al. (2), 2000. Preferably, the second order rate constant with respect to papain is at least about 10-fold, more preferably at least about 100-fold lower, than the second order rate constant for at least one Cathepsin. Examples for inhibitors of inhibitor of the protease activity of a Cathepsin B are Ac-Leu-Leu-NLe-H described in Schaschke et al., 1996, and 4-amino-azepan-3-one compounds disclosed in WO 2004/033445, the inhibitors summarized in Yasuda et al., 2005, in particular cathepsin inhibitor AAE581 (Balicatib), compound 462795 (relacatib), azepanones SB 331750 and SB 357114, inhibitor of cathepsin S MV57471, reversible aldehyde type inhibitors as described in Saegusa et al., 2002, Katunuma et al., 1999, Yasuma et al., 1998, and Katunuma et al., 2000; cyclic hydrazide compounds as disclosed in Duffy et al., 1999; reversible cylic ketone type inhibitors as described in Marquis et al. (1), 2001; Marquis et al., 1999, Marquis et al. (2), 2001, Marquis et al., 1998; reversible ketoamide type inhibitors as disclosed in Tavares et al. (1), 2004, Tavares et al. (2), 2004, Tavares et al. (3), 2004; reversible aminoethyl amide type inhibitors as disclosed in Altmann et al., 2002; reversible nitrile type inhibitors as disclosed in Greenspan et al., 2001, WO 01/58886, WO 02/20485, WO 01/09110, WO 01/19816, Robichaud et al., 2003, Ward et al., 2002; reversible cyanamide type inhibitors as disclosed in Falgueyret et al., 2001; beta-Lactam 6-substituted oxapenam compounds as disclosed in Zhou et al., 2002, and U.S. Pat. No. 5,905,076, beta-Lactam penam compounds as disclosed in U.S. Pat. No. 6,232,305 B1 and Zhou et al., 2002: beta-Lactam monobactam compounds as disclosed in Zhou et al., 2003, and U.S. Pat. No. 5,986,108; acrylamide compounds as disclosed in U.S. Pat. No. 6,635,621; pyrazole compounds as disclosed in Thurmond et al. (2), 2004, Thurmond et al. (3), 2004; epoxysuccinate compounds as disclosed in Katunuma et al., 2002; vinyl sulfone compounds as disclosed in Palmer et al., 1995, Bromme et al., 1996, McKerrow et al., 1999; diacyl hydroxamate compounds as disclosed in Bromme et al., 1989, Bromme et al., 1994; bis-hydrazides compounds as disclosed in Thompson et al., 1997, and Thompson et al., 1998,; acyclic ketone compounds as disclosed in Marquis et al., 1999, Huang et al., 2002, Shaw, 1994, Krantz, 1994, Smith et al., 2001, Seyfried et al., 2001; and beta-Lactam 2-substituted oxapenam compounds as disclosed in Zhou et al., 2001, and in U.S. Pat. No. 5,925,633; and the cathepsin inhibitors as summarized in Deaton and Kumar, 2004, in particular inhibitors of formula (1) to (273) disclosed therein. Preferred inhibitors of the protease activity of a Cathepsin are cathepsin inhibitors AAE581 (balicatib; N-[1-(cyanomethylcarbamoyl)cyclohexyl]-4-(4-propylpiperazin-1-yl)benzamide) and compound 462795 (relacatib; N-[(2S)-4-methyl-1-[[(4S,7R)-7-methyl-3-oxo-1-pyridin-2-ylsulfonyl-azepan-4-yl]amino]-1-oxopentan-2-yl]-1-benzofuran-2-carboxamide).

An "inhibitor of the protease activity of Cathepsin B" is understood as compound having a second order rate constant with respect to at least one Cathepsin of at least about $10^3$, preferably at least about $10^4$, more preferably at least about $10^5$, even more preferably at least about $10^6$ $k_2/k_1$ ($M^{-1}$ $s^{-1}$) as determined in an assay described in Schaschke et al. (2), 2000. Preferably, the second order rate constant with respect to papain is at least about 10-fold, more preferably at least about 100-fold lower, than the second order rate for at least one other Cathepsin. Preferably, the second order rate with respect to at least one other Cathepsin, in particular Cathepsin L, is at least about 10-fold, more preferably at least about 100-fold lower than the second order rate constant for Cathepsin B. In a preferred embodiment, the Cathepsin B is human Cathepsin B. In a preferred embodiment, the inhibitor of the protease activity of Cathepsin B is selected from NS-629, MeO-Gly-Gly-Leu-(2S,3S)-tEps-Leu-Pro-OH and $H_2N$—$(CH_2)_6$—NH-Gly-Gly-Leu-(2S,3S)-tEps-Leu-Pro-OH.

The "tumour stroma" is understood as cells and tissue components surrounding and interwoven with the tumour mass.

A "carrier" according to the present invention is understood a chemical entity which allows covalent or non-covalent binding of further moieties. In particular, the "carrier" according to the present invention is a nanodevice with a length in at least one dimension exceeding at least about 1 nm, preferably at least about 10 nm, more preferably at least about 100 nm, and which allows covalent or non-covalent binding of further moieties. In a preferred embodiment, the carrier is selected from a nanotube, a liposome, a lipoplex, a polymersome, a micell, a nanogel, a nanoparticle, a mesoporous silica particle, a dendrimer, and a nanoshell, in particular the carrier is a liposome, or other chemical entity that could be linked to the Cathepsin-binding compound. In a further preferred embodiment of the present invention, the carrier is selected from a nanotube, a liposome, a lipoplex, a polymersome, a micell, a nanogel, a nanoparticle, a mesoporous silica nanoparticle, a dendrimer, and a nanoshell, in particular the carrier is a liposome. In the case of a liposome, the therapeutic and/or diagnostic moiety may be encapsulated within the liposome, or the moiety may be bound via a lipid moiety to the membrane of the liposome. The generation of liposomes may be performed by methods known to a skilled person. In particular, the liposomes may be generated by extrusion as described in Example 3, or by sonification as described in Example 4. The Cathepsin-binding compound may be bound covalently or non-covalently to the carrier. As shown in Example 5, the Cathepsin-binding compound is in a preferred embodiment bound to the liposome non-covalently, in particular via a lipid moiety. In other embodiment, like e.g. dendrimers, the Cathepsin-binding compound and the therapeutic and/or diagnostic moiety are bound covalently to the dendrimer. The synthesis and use of a nanotube, a liposome, a lipoplex, a polymersome, a micell, a nanogel, a mesoporous silica nanoparticle, a dendrimer, and a nanoshell are for example described in Peer et al., 2007; Orive et al., 2009; Fahmy et al., 2007; Sun et al., 2008; and Ferrari, 2005.

Cathepsin-binding compounds may initially be chemically modified to enable further covalent or non-covalent coupling, in particular by introducing a linker. In one embodiment, the Cathepsin-binding compound is lipidated by introducing a lipid moiety, preferably via a linker, as for example shown in Example 1 and FIG. 2. Lipidation of a Cathepsin-binding compound allows easier coupling of such ligand to liposomes, micelles or lipoplexes, because of the lipid part a lipidated Cathepsin-binding compound can be added to the primary mixture in a carrier preparation. This method not only simplifies the coupling procedure but also excludes any manipulation of encapsulated compound.

Lipid vesicles are highly compatible with biological membranes in both composition and structure, and thus their use as delivery systems is well established. In this respect, liposomes loaded with at least one diagnostic or/and therapeutic moiety and bound to a Cathepsin-binding compound can be effective "drug carriers" for targeted delivery. This approach is very promising because, unlike magnetic targeting, it allows active targeting of the bionanocomposite to the site of choice, in particular tumour stroma and/or inflammation site, without the need for additional devices such as a source of the external magnetic field.

Suitable linkers are described in Quasba et al., 2008; Cruz et al., 2010; Rossin et al., 2005; Shuvaev et al., 2004; Liang et al., 2002 and Hylarides et al., 2001. In particular a functionalized PEG moiety and/or a diaminoalkyl moiety may be used as linker, as in NS-629.

Labelling of liposomes by use of a lipidated inhibitor is advantageous over other methods such as direct coupling of ligand to liposome surface by covalent coupling (U.S. Pat. No. 5,013,556) or attaching to the free ends of the polymer chains forming the surface coat on the liposomes (Allen et al., 1995; Blume et al., 1993). The lipid part of the developed inhibitor, hence, allows its incorporation in the lipid bilayer by adding the compound to the primary lipid mixture. Incorporation into the bilayer can in particular be performed by extrusion or sonification. Extrusion is exemplified in Example 3. Sonification is exemplified in Example 4.

A "liposome-binding compound" according to the present invention is understood as compound which is able to associate with liposomes covalently or non-covalently, preferably covalently. In particular, a liposome-binding compound comprises at least one lipid moiety which allows incorporation in the lipid bilayer of a liposome.

A "therapeutic moiety" according to the present invention is a chemical moiety, which is capable of exhibiting a therapeutic effect when administered to a patient in need thereof in an effective amount. The therapeutic moiety is preferably selected from:
  a toxin,
  a chemotherapeutic agent,
    in particular an alkylating agent and/or an anti-metabolite and/or a plant alkaloid and/or a taxane and/or a topoisomerase inhibitor and/or a antineoplastic agent
  a radioactive moiety,
  an apoptosis-inducing agent, and
  an anti-inflammatory agent,
    in particular a nonsteroidal anti-inflammatory agents, preferably selected from a salicylate, propionic acid derivative, acetic acid derivative, enolic acid derivative, and
    fenamic acid derivative, a selective COX-2 inhibitor, and a sulphonanilide, or
    in particular a steroidal anti-inflammatory agents, preferably a glucocorticoid.

It is understood, that the selection of the therapeutic moiety depends on the disease to be treated.

A "diagnostic moiety" according to the present invention is a chemical moiety, which can be detected. Preferably, the chemical moiety can be detected in vitro, ex vivo, or in vivo, preferably in vivo. The diagnostic moiety is preferably selected from:
  a radioactive label,
    in particular technetium-99m, iodine-123, iodine-131, rhenium-186, rhenium-188, gallium-67, yttrium-90, and lutetium-177,
  a paramagnetic agent,
    in particular a Gadolinium-complex, more preferably Gd-DTPA,
  a super paramagnetic nanoparticle,
    in particular iron oxide based nanoparticles,
  a PET-imageable agent,
  an MRI-imageable agent,
    in particular a Gadolinium-complex, more preferably Gd-DTPA,
  a fluorophore,
    in particular Alexa Fluor,
  a chromophore,
  a phosphorescing agent,
  a chemiluminescent agent, and
  a bioluminescent agent.

In some embodiments, a chemical moiety is both a diagnostic and a therapeutic moiety, as e.g. certain radioactive isotopes like iodine-123 and iodine-131.

In vivo detection and imaging can be performed for example with a magnetic resonance imaging (MRI) apparatus, in case an MRI or paramagnetic agent is to be detected, or with SPECT or PET cameras after accumulation of the radioactively labeled cathepsin-binding compound in the diseased tissue.

In one embodiment, the Cathepsin-binding compounds bound to a carrier comprising a therapeutic and/or diagnostic moiety and the Cathepsin-targeting compounds comprising a therapeutic and/or diagnostic moiety, may be administered as the only treatment, or may be used simultaneously with, before, or after different types of treatment, e.g. surgery, radiation; or may be administered to patients with, before, or after conventional chemotherapeutic, radiotherapeutic, anti-inflammatory or anti-angiogenic agents, or targeted immunotoxins or coaguligands. The compounds of a combinatory treatment may be administered to the patient simultaneously, either in a single composition, or as two distinct compositions using the same or different administration routes.

Figure 7:
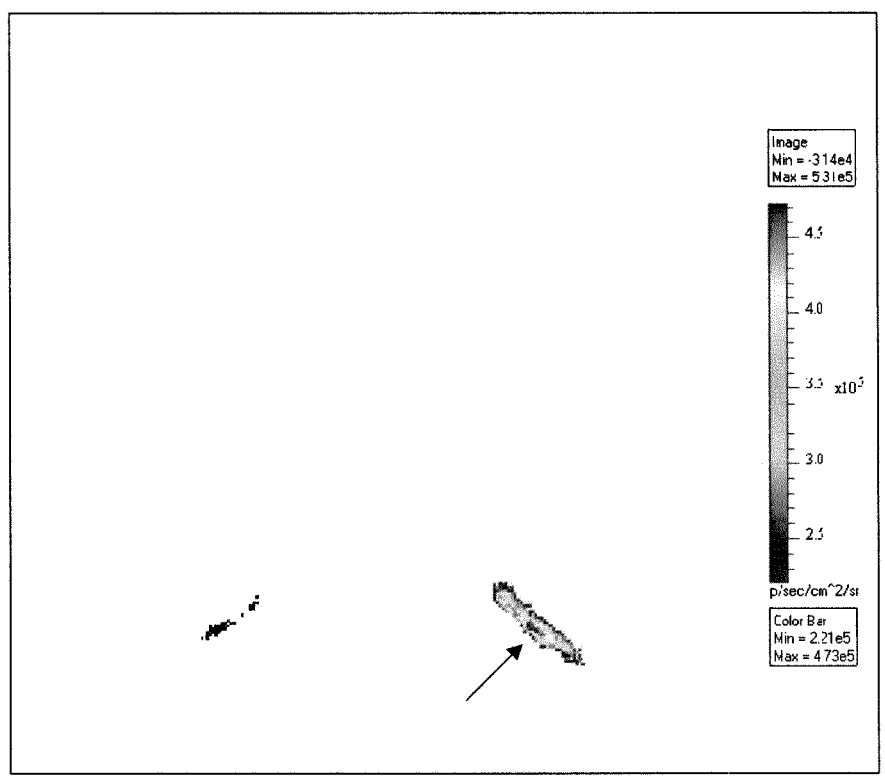

As shown in Example 9 and FIG. 7, the Cathepsin-binding compound of the invention surprisingly localizes in vivo at an inflammation area, namely a paw edema. Therefore, in one embodiment of the present invention, the invention relates to a Cathepsin-binding compound for use as described herein, wherein the use is a diagnostic use, and wherein the detection of a Cathepsin in vivo is indicative of an inflammatory site.

Cathepsin represents an early but dynamic target in inflammatory diseases and neoplastic diseases. A Cathepsin-binding compound as described herein can therefore be applied for example at multiple points in the treatment cascade of neoplastic diseases, from primary chemoprevention to treatment of relapsed and disseminated disease.

In a preferred embodiment, the neoplastic disease is selected from bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumours, germ cell tumour, extracranial cancer, Hodgkin's disease, acute lymphoblastic leukemia, acute myeloid leukemia, liver cancer, medulloblastoma, neuroblastoma, brain tumours, non-Hodgkin's lymphoma, mantle cell lymphoma, osteosarcoma, malignant fibrous histiocytoma of bone, retinoblastoma, rhabdomyosarcoma, soft tissue sarcomas, supratentorial primitive neuroectodermal pineal tumours, visual pathway and hypothalamic glioma, Wilms' tumour, acute lymphocytic leukemia, adult acute myeloid leukemia, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, and small-cell lung cancer, in particular lung cancer, non-small-cell lung cancer, prostate cancer, ovarian cancer, colorectal cancer, pancreatic cancer, breast cancer, glioblastoma, and metastasis thereof, more preferably breast cancer and metastasis thereof.

In a preferred embodiment, the inflammatory disease is selected from psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-hostdisease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, viral infections, cardiovascular diseases, ankylosing spondylitis, skin delayed type hypersensitivity disorders, Alzheimer's disease, systemic lupus erythematosus and allergic asthma, preferably selected from rheumatoid arthritis, Crohn's disease, ulcerative colitis, septic shock, psoriasis and atherosclerosis.

In another embodiment, the present invention relates to the use of a Cathepsin-binding compound bound to a carrier comprising a therapeutic and/or diagnostic moiety,
(i) for the preparation of a diagnostic and/or medicament for the diagnosis and/or treatment of inflammatory diseases,
and/or
(ii) for the preparation of a diagnostic and/or medicament for the diagnosis and/or treatment of neoplastic diseases, wherein the Cathepsin-binding compound binds to inflammatory cells of the tumour stroma.

In a further embodiment, the present invention relates to a method for diagnosing and/or treating an inflammatory disease, comprising administering an effective amount of a Cathepsin-binding compound bound to a carrier comprising a therapeutic and/or diagnostic moiety to a patient in need thereof.

In a further embodiment, the present invention relates to a method for diagnosing and/or treating neoplastic diseases, comprising administering an effective amount of a Cathepsin-binding compound bound to a carrier comprising a therapeutic and/or diagnostic moiety to a patient in need thereof, wherein the Cathepsin-binding compound binds to inflammatory cells of the tumour stroma.

Surprisingly, it could be shown in Examples 6 and 7, that the Cathepsin-binding compound NS-629 non-covalently bound to liposomes can surprisingly be used for binding to inflammatory cells. Moreover, it could surprisingly be shown in the Examples 8 and 9, that NS-629 bound to liposomes, wherein the liposomes carry a diagnostic label, like luciferine or the MRI agent Gd-DTPA, respectively, can be used for in vivo diagnosing inflammatory diseases, and/or neoplastic diseases, by binding to tumour stromal cells, and that the compound surprisingly targets to disease site in vivo (see also FIGS. 7 and 8). NS-629 is obtained by reacting H$_2$N—(CH$_2$)$_6$—NH-Gly-Gly-Leu-(2S,3S)-tEps-Leu-Pro-OH×TFA with DSPE-PEG(2000). The hexane-1,6-diamine moiety and the PEG moiety are part of the linker between the Cathepsin B-inhibitor moiety and the lipid moiety.

Therefore, in another embodiment, the present invention relates to a Cathepsin-binding and liposome-binding compound, comprising:
(i) a Cathepsin-binding moiety,
(ii) optionally a linker, and
(iii) a liposome-binding moiety.

In a preferred embodiment, the Cathepsin-binding and liposome-binding compound is a Cathepsin B-binding and liposome-binding compound and comprises:
(i) a Cathepsin B-binding moiety,
(ii) optionally a linker, and
(iii) a liposome-binding moiety.

In a further preferred embodiment, the Cathepsin-binding and liposome-binding compound is a Cathepsin S-binding and liposome-binding compound and comprises:
(i) a Cathepsin S-binding moiety,
(ii) optionally a linker, and
(iii) a liposome-binding moiety.

In a preferred embodiment, a Cathepsin-binding and liposome-binding compound, preferably a Cathepsin B-binding and liposome-binding compound of the invention or Cathepsin S-binding and liposome-binding compound of the invention has the structure of formula (IV):

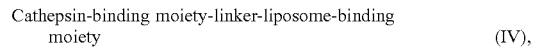

and in the case of a Cathepsin B-binding and liposome-binding compound,

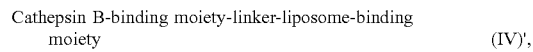

and in the case of a Cathepsin S-binding and liposome-binding compound,

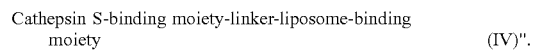

In a preferred embodiment, the Cathepsin-binding and liposome-binding compound, preferably the Cathepsin B-binding and liposome-binding compound comprises a linker, even more preferably the linker comprises a functionalized PEG moiety and/or a diaminoalkyl moiety. The diaminoalkyl moiety is preferably a moiety having the structure —HN—(CH$_2$)$_1$—NH— wherein 1 is an integer from n=2 to 30, preferably 3 to 20, most preferably n=6.

In a further preferred embodiment, the linker in the Cathepsin-binding and liposome-binding compound, preferably the Cathepsin B-binding and liposome-binding compound has the structure of formulas II to V:

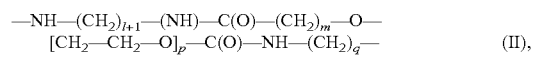

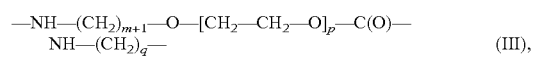

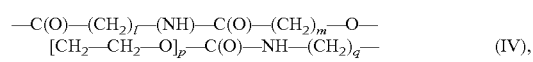

and

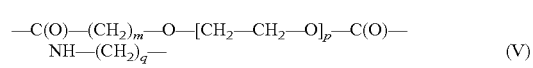

wherein
1 is an integer from n=1 to 30, preferably 3 to 20, most preferably n=5, m is an integer from n=1 to 30, more preferably 1 to 10, most preferably 1, p is an integer from n=1 to 200, more preferably 15 to 100, most preferably 38 to 53, q is an integer from n=2 to 30, more preferably 2 to 10, most preferably 2.

In a preferred embodiment, the liposome-binding moiety of the Cathepsin binding and liposome-binding compound, preferably the Cathepsin B-binding and liposome-binding compound of the invention is a phospholipid, in particular a phospholipid comprising 1, 2 or more stearoyl moieties, 1, 2 or more oleyl moieties, 1, 2 or more lauroyl moieties, 1, 2 or more myristoyl moieties, 1, 2 or more palmitoyl moieties, and/or 1, 2 or more arachinoyl moieties, more preferably a phospholipid comprising 2 stearoyl moieties.

In a more preferred embodiment, the Cathepsin B-binding and liposome-binding compound of the invention has the structure of formula (XIII):

-Gly-Aaa-Bbb-X-Ccc-Ddd    (VI),

-Gly-Aaa-Bbb-X-Ccc    (VII)

and

-Gly-Aaa-Bbb-Y    (VIII), wherein

X is an electrophilic unit, in particular an epoxide-derivative or a semicarbazide-derivative, preferably tEps, —(NH)—(NH)—C(O)—, most preferably (2S,3S)-tEps;

Y is an electrophilic unit, in particular an epoxide-derivative, a semicarbazide-derivative or a nitrile-derivative, preferably -tEps, —(NH)—(NH)—C(O)—NH$_2$, —(NH)—CH$_2$—CN, more preferably (2S,3S)-tEps;

Aaa is selected from the group consisting of Gly, Phe, Asp, Glu, 1-aminoadipic acid, in particular Gly;

Bbb is selected from the group consisting of aliphatic or aromatic hydrophobic amino acids, in particular Leu, Ile, Phe, Tyr, Val,

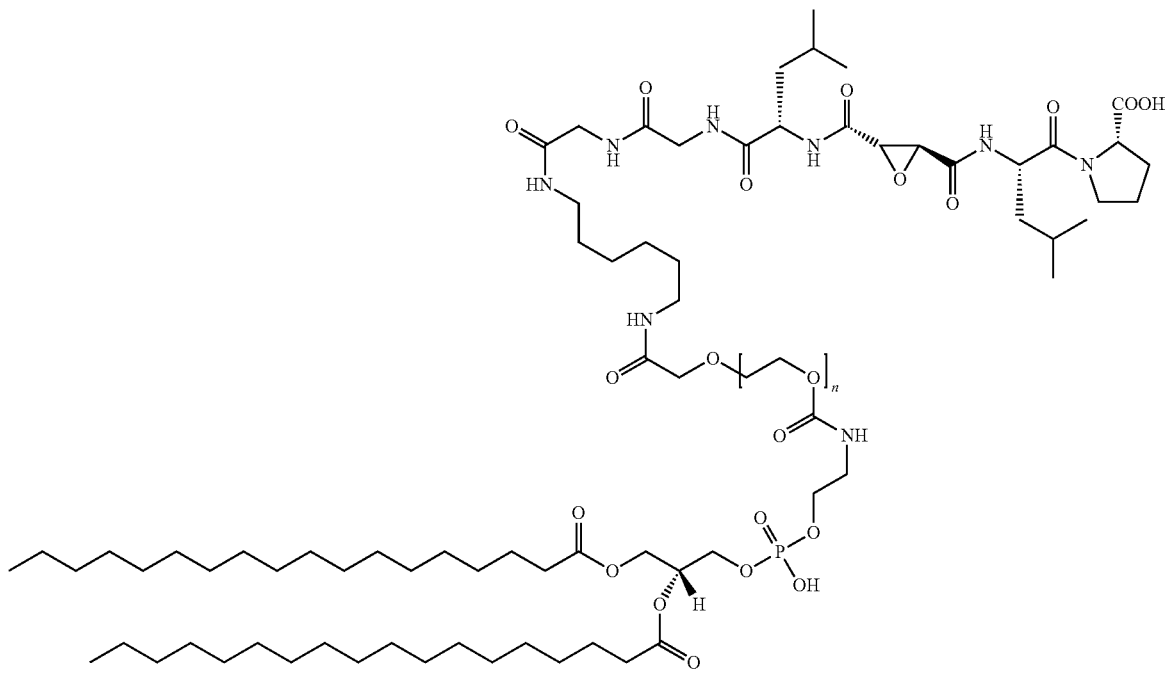

(XIII)

wherein n=38 to 53.

It is understood, that in a preparation, various lengthes of the PEG moiety may be present. Preferably, the most abundant PEG species has n=45 or n=46. Thus, in a further preferred embodiment, the invention relates to a mixture Cathepsin B-binding and liposome-binding compounds of the invention of formula (XIII), wherein the n in the compounds are 2 or more different integers from 38 to 53.

In a further preferred embodiment, the Cathepsin-binding and liposome-binding compound of the invention comprises a Cathepsin-binding moiety, wherein the Cathepsin-binding moiety is an inhibitor of the protease activity of Cathepsin. The Cathepsin-binding moiety is in particular a peptide inhibitor.

The Cathepsin-binding moiety is preferably selected from the group consisting of:

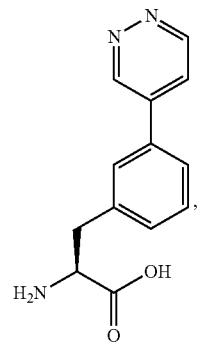

(IX)

-continued

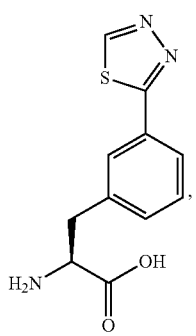

(X)

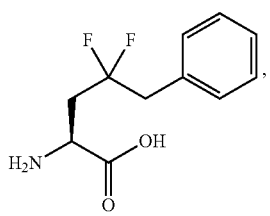

(XI)

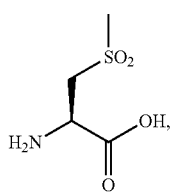

(XII)

2-naphthyl alanine, cyclohexyl alanine, 4-bromophenyl alanine, preferably amino acids (IX), (X), (XI), (XII), 2-naphthyl alanine, cyclohexyl alanine, 4-bromophenyl alanine, Leu, Ile, Phe, Tyr, more preferably amino acids (IX), (X), (XI), (XII), 2-naphthyl alanine, cyclohexyl alanine, 4-bromophenyl alanine, Leu and Ile;

Ccc is selected from the group consisting of aliphatic or aromatic hydrophobic amino acids, in particular Leu, Ile, Phe, Tyr, Val, Trp, Nle, preferably Nle and Leu, more preferably Leu;

Ddd is selected from the group consisting of aliphatic or aromatic hydrophobic amino acids and amino compounds, in particular Trp, Val, Ile, Phe, Tyr, Ala, Ser, Thr, Pro, —NH($CH_2$)$_{n=0-4}$—$CH_3$, —NH—CH($CH_3$)$_2$, —NH—$CH_2$—CH($CH_3$)$_2$, —NH—($CH_2$)$_{n=1-2}$Ph, preferably, Trp, Val, Ile, Phe, Tyr, more preferably Trp.

In preferred embodiments, the electrophilic units X and Y are epoxide-derivatives. A preferred epoxide-derivative according to the invention is tEps, wherein tEps is available in several stereoisomers. Preferable steroisomers are (2S,3S)-tEps and (2R,3R)-tEps, wherein (2S,3S)-tEps is more preferred.

In a preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-X-Ccc-Ddd, wherein X is (2S,3S)-tEps and Aaa, Bbb, Ccc and Ddd are selected from the group consisting of aliphatic amino acids, preferably from the group consisting of aliphatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-X-Ccc-Ddd, wherein X is —(NH)—(NH)—C(O)— and Aaa, Bbb, Ccc and Ddd are selected from the group consisting of aliphatic amino acids, preferably from the group consisting of aliphatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-X-Ccc-Ddd, wherein X is (2S,3S)-tEps and Aaa, Bbb, Ccc and Ddd are selected from the group consisting of aromatic amino acids, preferably from the group consisting of aromatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-X-Ccc-Ddd, wherein X is —(NH)—(NH)—C(O)— and Aaa, Bbb, Ccc and Ddd are selected from the group consisting of aromatic amino acids, preferably from the group consisting of aromatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-Y, wherein Y is (2S,3S)-tEps and Aaa, Bbb are selected from the group consisting of aliphatic amino acids, preferably from the group consisting of aliphatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-Y, wherein Y is —(NH)—(NH)—C(O)—$NH_2$ and Aaa, Bbb are selected from the group consisting of aliphatic amino acids, preferably from the group consisting of aliphatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-Y, wherein Y is (2S,3S)-tEps and Aaa, Bbb are selected from the group consisting of aromatic amino acids, preferably from the group consisting of aromatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-Y, wherein Y is —(NH)—(NH)—C(O)—$NH_2$ and Aaa, Bbb are selected from the group consisting of aromatic amino acids, preferably from the group consisting of aromatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-Y, wherein Y is —(NH)—$CH_2$—CN and Aaa, Bbb are selected from the group consisting of aliphatic amino acids, preferably from the group consisting of aliphatic hydrophobic amino acids.

In a further preferred embodiment, the Cathepsin-binding moiety, preferably the Cathepsin B-binding moiety or Cathepsin S-binding moiety, most preferably the Cathepsin B-binding moiety, is a peptide inhibitor represented by the formula -Gly-Aaa-Bbb-Y, wherein Y is —(NH)—$CH_2$—CN and Aaa, Bbb are selected from the group consisting of aromatic amino acids, preferably from the group consisting of aromatic hydrophobic amino acids.

In a further embodiment according to the invention, the Cathepsin-binding and liposome-binding compound is a Cathepsin B-binding moiety and is an inhibitor of the protease activity of Cathepsin B. The Cathepsin B-binding moiety is in particular a peptide inhibitor, preferably a peptide inhibitor selected from the group consisting of -Gly-Aaa-Bbb-X-Ccc-Ddd  (VI), and -Gly-Aaa-Bbb-X-Ccc  (VII), wherein X, Aaa, Bbb, Ccc and Ddd have the meanings as described below.

In a preferred embodiment X is an electrophilic unit, in particular an epoxide-derivative or a semicarbazide-derivative, preferably tEps or —(NH)—(NH)—C(O)—, most preferably (2S,3S)-tEps.

In a further preferred embodiment Aaa is an aliphatic amino acid of the general formula $NH_2$—CHR—COOH, wherein R is preferably selected from the group consisting of hydrogen, methyl or isopropyl. In a preferred embodiment R is hydrogen and therefore Aaa is Gly.

In a further preferred embodiment Bbb is selected from the group consisting of aliphatic or aromatic hydrophobic amino acids, in particular Leu, Ile, Phe, Tyr, Val, preferably Leu, Ile, Phe, Tyr, more preferably Leu and Ile;

According to the invention Ccc is preferably selected from the group consisting of aliphatic or aromatic hydrophobic amino acids, in particular Leu, Ile, Val, Nle, preferably Nle and Leu, more preferably Leu;

In another preferred embodiment Ddd is selected from the group consisting of aliphatic or aromatic hydrophobic amino acids and amino compounds, in particular Trp, Val, Ile, Phe, Tyr, Ala, Ser, Thr, Pro, preferably, Trp, Val, Ile, Phe, Tyr, more preferably Trp.

Preferred embodiments of the Cathepsin-binding moiety, in particular of the Cathepsin B-binding moiety are -Gly-Gly-Leu-(2S,3S)-tEps-Leu-Pro-OH, -Gly-Gly-Leu-(2S,3S)-tEps-Leu-Trp-OH, -Gly-Gly-Leu-(2S,3S)-tEps-Nle-Pro-OH, -Gly-Gly-Ile-(2S,3S)-tEps-Leu-Pro-OH, -Gly-Gly-Ile-(2S,3S)-tEps-Leu-Trp-OH, -Gly-Gly-Ile-(2S,3S)-tEps-Nle-Trp-OH, more preferably are the moieties -Gly-Gly-Leu-(2S,3S)-tEps-Leu-Pro-OH and -Gly-Gly-Leu-(2S,3S)-tEps-Leu-Trp-OH, most preferably -Gly-Gly-Leu-(2S,3S)-tEps-Leu-Pro-OH. According to the invention, —OH represents that the amino acid is present as free acid.

In a further embodiment according to the invention, the Cathepsin-binding and liposome-binding compound is a Cathepsin S-binding moiety and is an inhibitor of the protease activity of Cathepsin S. The Cathepsin S-binding moiety is in particular a peptide inhibitor, preferably a peptide inhibitor selected from the group consisting of -Gly-Aaa-Bbb-X-Ccc-Ddd  (VI), -Gly-Aaa-Bbb-X-Ccc  (VII)

and

-Gly-Aaa-Bbb-Y  (VIII), wherein X, Y, Aaa, Bbb, Ccc and Ddd have the meanings as described below.

In a preferred embodiment X is an electrophilic unit, in particular an epoxide-derivative or a semicarbazide-derivative, preferably tEps or —(NH)—(NH)—C(O)—, most preferably (2S,3S)-tEps.

In a further preferred embodiment Y is an electrophilic unit, in particular an epoxide-derivative, a semicarbazide-derivative or a nitrile-derivative. Preferably, Y is tEps, —(NH)—(NH)—C(O)—$NH_2$, —(NH)—$CH_2$—CN, more preferably (2S,3S)-tEps.

In a further preferred embodiment Aaa is an aliphatic, aromatic or acidic α-amino acid. Aaa is preferably selected from the group consisting of Gly, Phe, Asp, Glu, 1-aminoadipic acid, wherein Gly is most preferred.

In a further preferred embodiment Bbb is selected from the group consisting of aliphatic or aromatic hydrophobic amino acids. In particular Bbb is selected from the group of proteinogenic amino acids consisting of Leu, Ile, Phe, Tyr, Val or selected from the group of non-proteinogenic amino acids consisting of 2-naphthyl alanine, cyclohexyl alanine, 4-bromophenyl alanine or selected from the group of non-proteinogenic amino acids with the formulas:

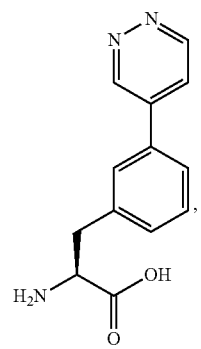

(IX)

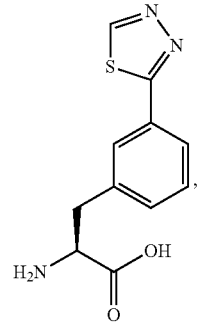

(X)

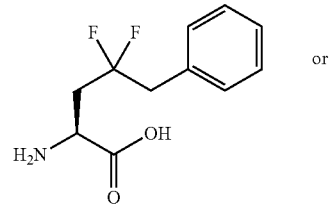

(XI)

or

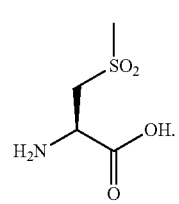

(XII)

Bbb is more preferably selected from the group of 2-naphthyl alanine, cyclohexyl alanine, 4-bromophenyl alanine, Leu, Ile, Phe, Tyr and amino acids (IX), (X), (XI) or (XII). Most preferably, Bbb is selected from the group of amino acids (IX), (X), (XI) or (XII), 2-naphthyl alanine, cyclohexyl alanine, 4-bromophenyl alanine and Leu.

In a further preferred embodiment, Ccc is selected from the group consisting of aliphatic or aromatic hydrophobic amino acids, in particular Leu, Ile, Phe, Tyr, Val, Trp, preferably Leu and Ile, more preferably Leu.

In another preferred embodiment Ddd is an amino compound, in particular an alkyl amino compound, an alkaryl amino compound or an aryl amino compound, in particular —NH(CH$_2$)$_{n=0-4}$—CH$_3$, —NH—CH(CH$_3$)$_2$, —NH—CH$_2$—CH(CH$_3$)$_2$, —NH—(CH$_2$)$_{n=1-2}$Ph.

Preferred embodiments of the Cathepsin-binding moiety, in particular of the Cathepsin S-moiety are -Gly-Gly-Leu-(2S,3S)-tEps-Leu-OH, -Gly-Glu-Leu-(2S,3S)-tEps-Leu-OH, -Gly-Glu-Leu-(2S,3S)-tEps-Ile-OH, -Gly-Gly-Leu-(2S,3S)-tEps-Leu-NH—CH$_2$—CH$_3$, more preferably is the moiety -Gly-Glu-Leu-(2S,3S)-tEps-Leu-NH—CH$_2$—CH$_3$, -Gly-Gly-Xxx-(2S,3S)-tEps-Leu-NH—CH$_2$—CH$_3$, where Xxx represents an amino acid with the formula (IX) or (X). According to the invention, —OH represents that the amino acid is present as free acid.

Further examples of preferred Cathepsin S-moieties are:

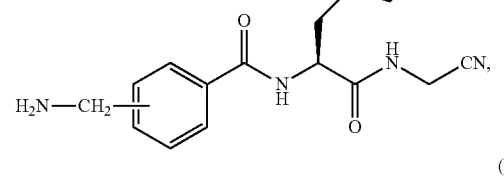

(XIII)

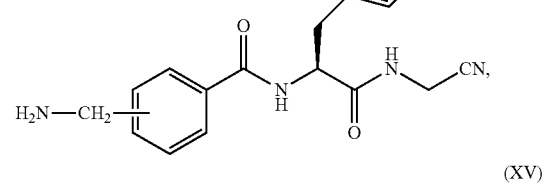

(XIV)

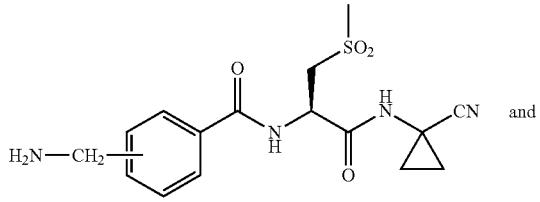

(XV)

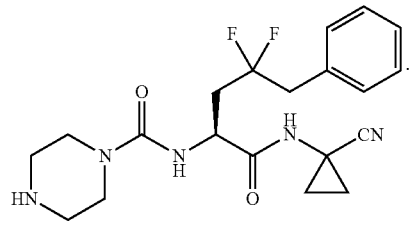

(XVI)

In formulas (XIII), (XIV) and (XV) the phenyl-ring can be substituted in ortho-, meta or para-position.

In preferred embodiments of the invention, the Cathepsin-binding and liposome-binding compound, in particular the Cathepsin B-binding and liposome-binding compound and Cathepsin S-binding and liposome-binding compound, more preferably the Cathepsin B-binding and liposome-binding compound comprises next to the Cathepsin-binding moiety a linker.

In embodiments of the present invention in which the electrophilic unit X and/or Y of the Cathepsin-binding moiety is an epoxide-derivative, the linker is preferably selected from

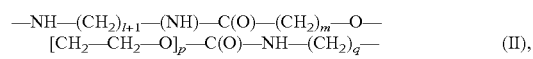

(II), and/or

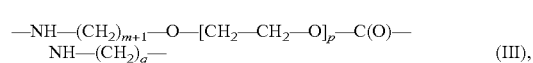

(III), wherein
l is an integer from n=1 to 30, preferably 3 to 20, most preferably n=5,
m is an integer from n=1 to 30, more preferably 1 to 10, most preferably 1,
P is an integer from n=1 to 200, more preferably 15 to 100, most preferably 38 to 53,
q is an integer from n=2 to 30, more preferably 2 to 10, most preferably 2.

In embodiments of the present invention in which the electrophilic unit X and/or Y of the Cathepsin-binding moiety is a semicarbazide-derivative or nitrile-derivative, the linker is preferably selected from

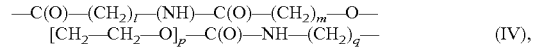

(IV), and/or

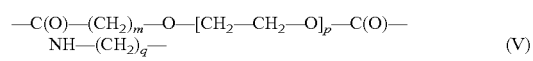

(V)

wherein
l is an integer from n=1 to 30, preferably 3 to 20, most preferably n=5,
m is an integer from n=1 to 30, more preferably 1 to 10, most preferably 1,
p is an integer from n=1 to 200, more preferably 15 to 100, most preferably 38 to 53,
q is an integer from n=2 to 30, more preferably 21 to 10, most preferably 2.

The invention further relates to a Cathepsin-targeting, in particular to a Cathepsin B-targeting compound or Cathepsin-S-targeting compound, comprising a Cathepsin-binding and liposome-binding compound of the invention, in particular a Cathepsin B-binding and liposome-binding compound of the invention or Cathepsin S-binding and liposome-binding compound of the invention, bound to a liposome.

The invention further relates to a Cathepsin targeting compound, further comprising a therapeutic and/or diagnostic moiety.

The invention further relates to a Cathepsin B-targeting compound, further comprising a therapeutic and/or diagnostic moiety.

In a preferred embodiment, the Cathepsin targeting compound of the invention, or the Cathepsin binding and liposome-binding compound of the invention comprise a cathepsin-binding compound, which is an inhibitor of the protease activity of Cathepsin, in particular a peptide inhibitor, more preferably the moiety -Gly-Gly-Leu-(2S,3S)-tEps-Leu-Pro-OH.

In a preferred embodiment, the Cathepsin B-targeting compound of the invention, or the Cathepsin B-binding and liposome-binding compound of the invention comprise a cathepsin-binding compound, which is an inhibitor of the protease activity of Cathepsin B, in particular a peptide inhibitor, more preferably the moiety -Gly-Gly-Leu-(2S, 3S)-tEps-Leu-Pro-OH.

In a preferred embodiment, the Cathepsin targeting compound of the invention, in particular the Cathepsin B-targeting compound of the invention or the Cathepsin S-targeting compound of the invention, comprises a diagnostic moiety, wherein the diagnostic moiety is preferably selected from:
  a radioactive label,
  a paramagnetic agent,
    in particular a Gadolinium-complex, more preferably Gd-DTPA,
  a super paramagnetic nanoparticle,
    in particular iron oxide based nanoparticles,
  a PET-imageable agent,
  an MRI-imageable agent,
    in particular a Gadolinium-complex, more preferably Gd-DTPA,
  a fluorophore,
    in particular Alexa Fluor,
  a chromophore,
  a phosphorescing agent,
  a chemiluminescent agent, and
  a bioluminescent agent.

In a preferred embodiment, the Cathepsin targeting compound of the invention comprises a therapeutic moiety,
  wherein the therapeutic moiety is preferably selected from:
    a toxin,
    a chemotherapeutic agent,
      in particular an alkylating agent or/and an antimetabolite or/and a plant alkaloid or/and a taxane or/and a topoisomerase inhibitor or/and a antineoplastic agent
    a radioactive moiety,
    an apoptosis-inducing agent, and
    an anti-inflammatory agent,
      in particular a non-steroidal anti-inflammatory agents,
        preferably selected from a salicylate, propionic acid derivative, acetic acid derivative, enolic acid derivative, and
        fenamic acid derivative, a selective COX-2 inhibitor, and a sulphonanilide, or
      in particular a steroidal anti-inflammatory agents, preferably a glucocorticoids.

The invention further relates to a Cathepsin targeting compound of the invention, in particular to a Cathepsin B-targeting compound of the invention or a Cathepsin S-targeting compound of the invention,
  (i) for use in the diagnosis of inflammatory diseases, and/or
  (ii) for use in the diagnosis of neoplastic diseases, wherein the Cathepsin-targeting moiety binds to inflammatory cells of the tumor stroma, in particular in breast neoplastic disease.

"bound to" according to the present invention is understood as being covalently or non-covalently bound. In the case of non-covalent binding, e.g. hydrophobic forces may ensure stable binding, for example by a lipid anchor inserted into a lipid bilayer, as shown in the Examples.

In a preferred embodiment, the Cathepsin-binding and liposome-binding compound of the invention is non-covalently bound to a liposome.

In a preferred embodiment, the Cathepsin B-binding and liposome-binding compound of the invention is non-covalently bound to a liposome.

In a further preferred embodiment, the Cathepsin binding moiety of the invention is covalently coupled to a lipid or lipid derivative via a linker. As in FIG. 1, the linker may comprise $\epsilon$-aminohexanoic acid and a functionalized PEG moiety.

In a further preferred embodiment, the Cathepsin B-binding moiety of the invention is covalently coupled to a lipid or lipid derivative via a linker. As in FIG. 1, the linker may comprise $\epsilon$-aminohexanoic acid and a functionalized PEG moiety.

In a further preferred embodiment, the a Cathepsin binding moiety is an inhibitor of the protease activity of Cathepsin. As shown in the examples, NS-629 may be used. In a further preferred embodiment, the Cathepsin-targeting compound comprises NS-629 bound to a liposome.

In a further preferred embodiment, the a Cathepsin B-binding moiety is an inhibitor of the protease activity of Cathepsin B. As shown in the examples, NS-629 may be used. In a further preferred embodiment, the Cathepsin B-targeting compound comprises NS-629 bound to a liposome.

In a further embodiment, the present invention relates to a method for diagnosing and/or treating an inflammatory disease, comprising administering an effective amount of a Cathepsin-targeting compound of the invention comprising a therapeutic and/or diagnostic moiety to a patient in need thereof.

In a further embodiment, the present invention relates to a method for diagnosing and/or treating neoplastic diseases, comprising administering an effective amount of a Cathepsin-targeting compound to a patient in need thereof, wherein the Cathepsin-binding moiety binds to inflammatory cells of the tumour stroma.

In a preferred embodiment, the compounds and compounds for use are administered as a pharmaceutical composition.

The pharmaceutical composition of the present invention contains therapeutically and/or diagnostically effective amounts of the individual compounds of the invention and generally an acceptable pharmaceutical "drug carrier", diluent or excipient, e.g. sterile water, physiological saline, bacteriostatic saline, i.e. saline containing about 0.9% mg/ml benzyl alcohol, phosphate-buffered saline, Hank's solution, Ringer's-lactate, lactose, dextrose, sucrose, trehalose, sorbitol, mannitol, and the like. The composition is generally a solution or suspension. It can be administered systemically, intravenously, orally, subcutaneously, intramuscularly, pulmonary, by inhalation and/or through sustained release administrations. Preferably, the composition is administered systemically, in particular intravenously.

The term "therapeutically effective amount" generally means the quantity of a compound of the invention which results in the desired therapeutic effect. A typical dosage range is from about 0.01 mg 1000 mg per application.

The term "diagnostically effective amount" generally means the quantity of a compound of the invention which results in the desired diagnostic effect without causing unacceptable side-effects. A typical dosage range is from about 0.01 mg 1000 mg per application. An advantage of the invention is that low dosages can be used and therefore compounds of the invention e.g. can hardly be detected 24 hours after administration.

Generally, the application of the pharmaceutical composition to a patient is one or several times per day, or one or several times a week, or even during longer time periods as the case may be.

The invention further relates to a method for preparing a Cathepsin-binding and liposome-binding compound, comprising providing a Cathepsin-binding moiety and associating a liposome-binding moiety, in particular associating a linker and a liposome-binding moiety with the Cathepsin-binding moiety. Preferably, the Cathepsin-binding moiety and/or the linker and/or the liposome-binding moiety are connected by chemical synthesis known to a person skilled in the art. In a further embodiment the Cathepsin-binding moiety and/or the linker and/or the liposome-binding moiety are protected by appropriate protecting groups. Examples of protecting groups are for amines BOC, Cbz or Fmoc, for alcohols are MOM or THP and for carboxygroups are Bn or methyl. Further protecting groups are possible, too, and are known to a person skilled in the art.

FIGURES

FIG. 1: Preferred embodiment of the present invention. A, cathepsins are normally localized in the intracellular organelles: endosomes or lysosmes. However, in several pathological conditions cathepsins could be translocated to the extracelluar milieu. B, An example of the cathepsin-binding compounds bound to a carrier, represented as LNP—NS-629. NS-629 represents the preferred Cathepsin-binding and liposome-binding compound according to formula (III), wherein n=38 to 53. In exemplary embodiments, the cathepsin-binding compounds bound to a carrier are 90-110 nm. C, Targeting system based on cathepsin-binding compounds binding to extracellular cathepsins enabling active targeting of encapsulated drug.

Figure 2:
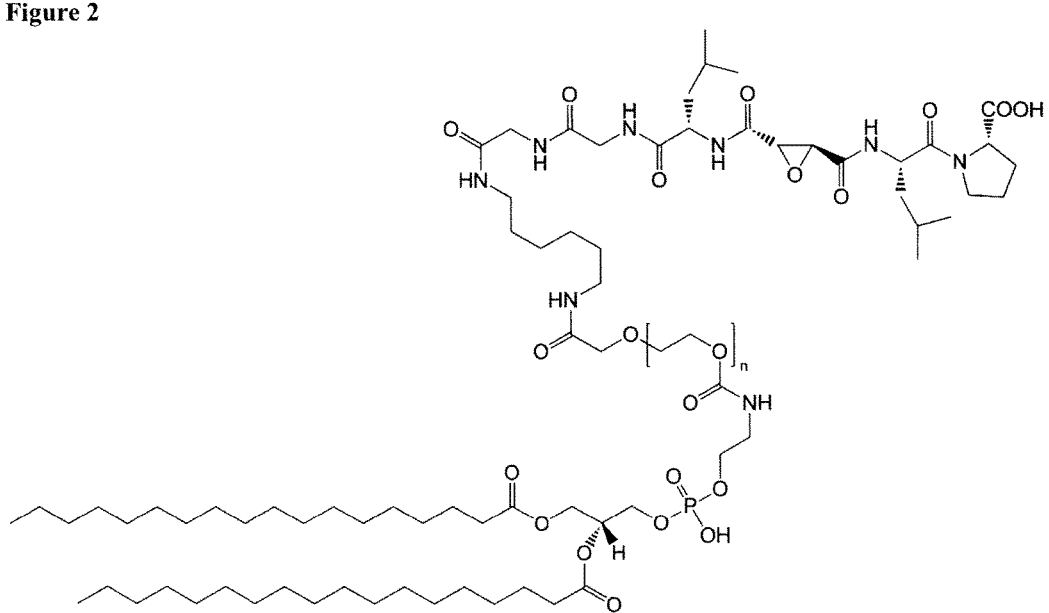

FIG. 2: Chemical structure of the lipidated inhibitor NS-629 (length distribution of the PEG segment: n=38-53).

Figure 3:
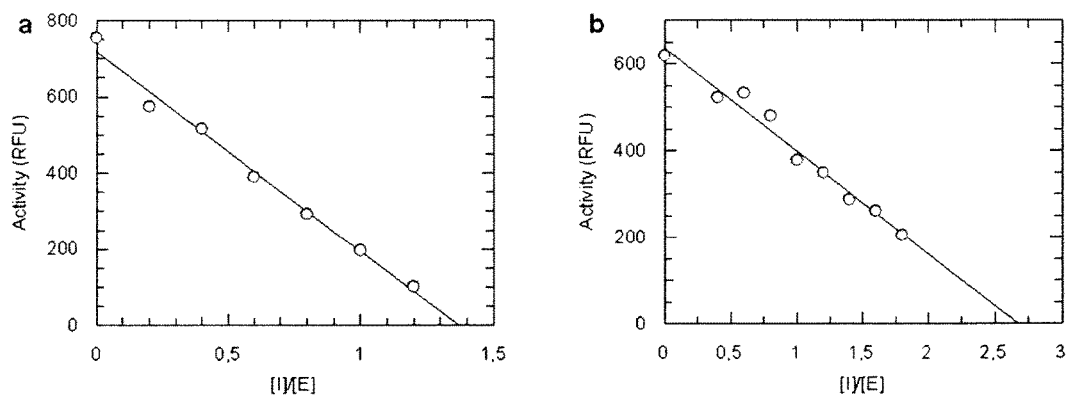

FIG. 3: Titration of Cathepsin B with free NS-629 (a) and liposome-coupled lipidated NS-629 (b) at pH 6.0 and 25° C. The solid lines were generated by linear regression analysis.

Figure 4:
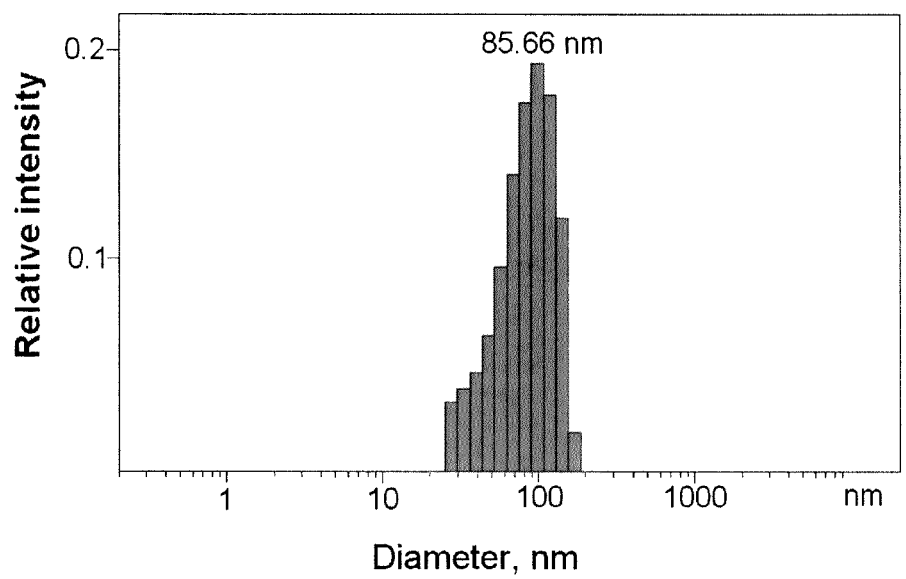

FIG. 4: Size distribution of liposomes functionalized with lipidated inhibitor as determined by dynamic light scattering (DLS). Average size is 85.66 nm.

Figure 5:
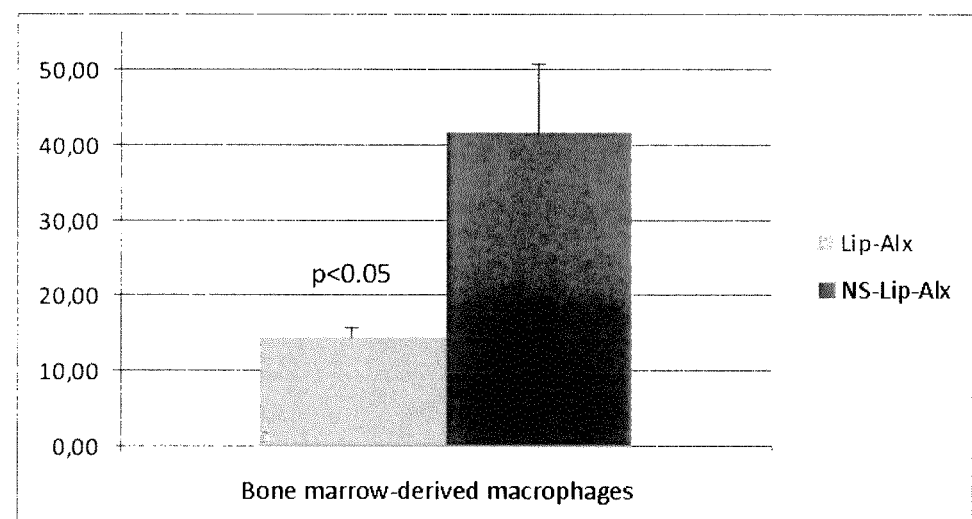

FIG. 5: Validation of targeting of liposomes with lipidated Cathepsin inhibitor to the immune cells. Liposomes functionalized (NS-Lip-Alx) and not functionalized (Lip-Alx) with NS-629 were loaded with fluorescence marker (Alexa Fluor 546™; (Invitrogen)) and incubated with mouse bone marrow-derived macrophages for 15 minutes at 4° C. Fluorescence of accumulated marker was measured with TECAN plate reader. As a control liposomes without labeling were used.

Figure 6:
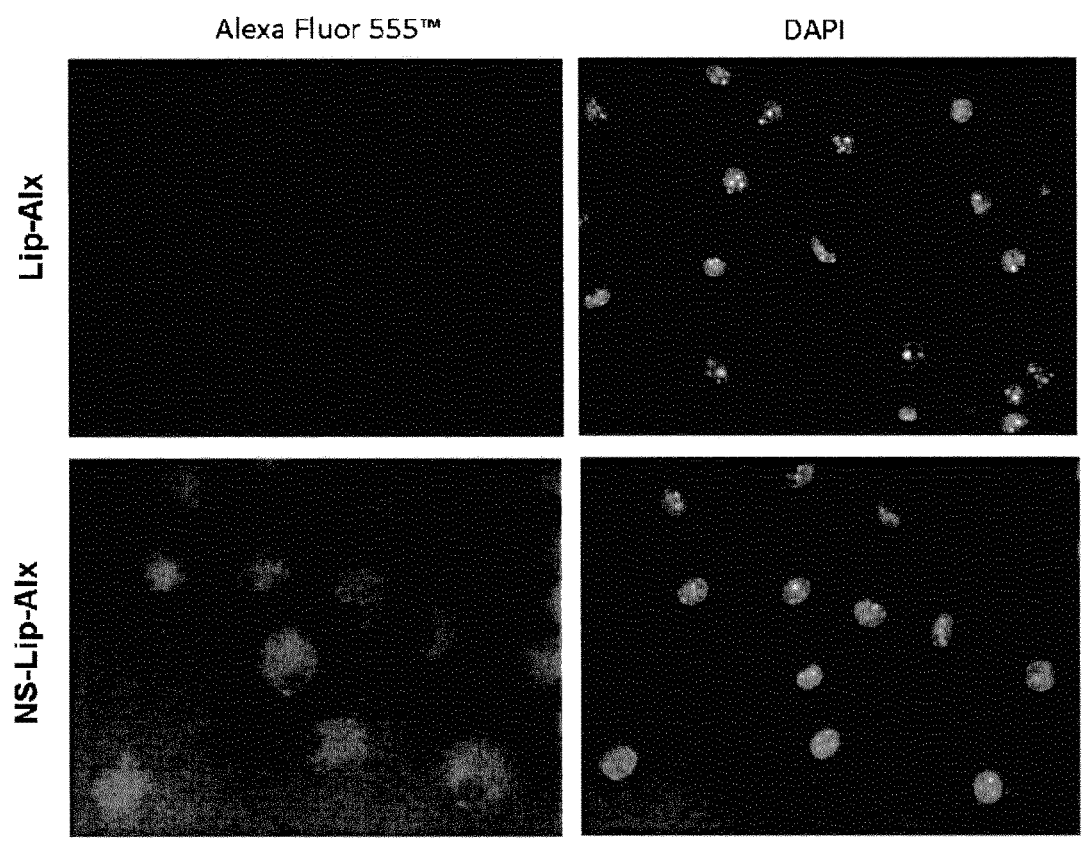

FIG. 6: Representation of liposomes with lipidated Cathepsin inhibitor targeting efficiency in primary mouse immune cells.

Non-functionalized liposomes (Lip-Alx) and liposomes functionalized with NS-629 (NS-Lip-Alx) were loaded with fluorescence marker (Alexa Fluor 555™ (Invitrogen)) and incubated with mouse bone marrow-derived macrophages for 15 minutes at 4° C. Fluorescence of accumulated marker was examined with an Olympus fluorescence microscope (Olympus IX 81) with Imaging Software for Life Science Microscopy Cell$^R$.

FIG. 7: Targeted delivery of liposomes labeled by lipidated inhibitor carrying D-luciferin into transgenic mouse expressing luciferase (FVB.luc$^{rg/+}$). The high-intensity luciferase signal associated with the induced paw edema demonstrates selective accumulation of labelled liposomes in the inflammation area. The scale is in photons/sec/sm$^2$/sr.

Figure 8:
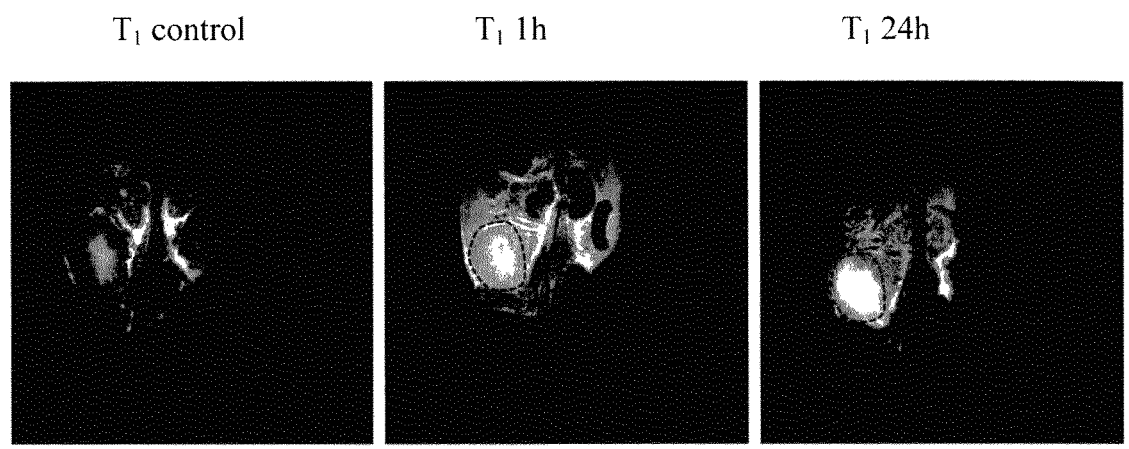

FIG. 8: $T_1$-weighted MR images (TE=8.5 ms, TR=400 ms) of an orthotopic transplanted breast cancer mouse before, 1 and 24 hours after ($T_1$) intraperitoneal injection of 200 μl NS-629 labeled liposomes containing Magnevist® (Bayer HealthCare Pharmaceuticals). The tumour tissue possess negative MR signal on $T_1$-weighted images. The bright signal at 1 and 24 hours after injection in $T_1$-weighted MR image indicates successful targeting of Magnevist® (Bayer HealthCare Pharmaceuticals) loaded NS-629 labelled liposomes.

EXAMPLES

Example 1

Synthesis of the Lipidated Inhibitor NS-629

DSPE-PEG(2000) refers to 1,2-distearoyl-sn-glycero-3-phosphoethanolamine-N-[carboxy(polyethylene glycol)-2000] (ammonium salt) (CAS Reg. 474922-20-8). DSPE-PEG(2000) carboxylic acid with PEG unit length of n=45 (PEG lengthes of n=38 to 53 are present) has the following formula I:

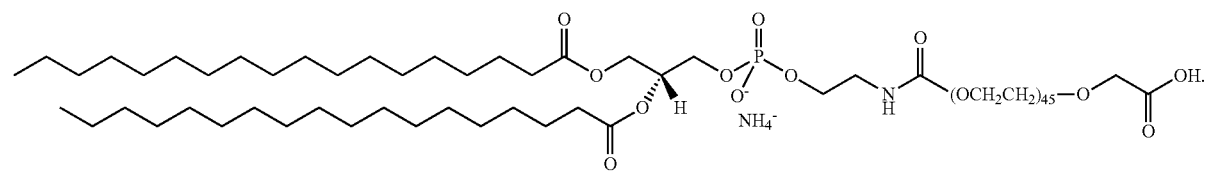

(I)

DSPE-PEG(2000) carboxylic acid (Avanti Polar Lipids, Inc.) (30.0 mg, 10.5 µmol) was suspended in MeCN (1 mL) and CHCl$_3$ was added dropwise until a clear solution was obtained. Then at room temperature under stirring a solution of DSC (Fluka, Buchs) in MeCN (c=0.0105 mol/L, 1 mL) and a solution of DIPEA in MeCN (c=0.105 mol/L, 0.1 mL) were added. In parallel, H$_2$N—(CH$_2$)$_6$—NH-Gly-Gly-Leu-(2S,3S)-tEps-Leu-Pro-OH×TFA (16.5 mg, 21 µmol; prepared by treating H$_2$N—(CH$_2$)$_6$—NH-Gly-Gly-Leu-(2S,3S)-tEps-Leu-Pro-OtBu (Schaschke et al. (1), 2000) with TFA/H$_2$O (95:5, v/v)) was suspended in MeCN (1 mL) and H$_2$O was added dropwise until a clear solution was obtained. H$_2$N—(CH$_2$)$_6$—NH-Gly-Gly-Leu-(2S,3S)-tEps-Leu-Pro-OH×TFA and its synthesis are described in Schaschke et al. (2), 2000, and in Schaschke et al., 1998. Then to this solution a solution of DIPEA in MeCN (c=0.105 mol/L, 0.4 mL) was added. After 60 min, this solution was added to the formed active ester of DSPE-PEG(2000) carboxylic acid and stirring was continued for 48 h. The solvent was evaporated under reduced pressure and the resulting material was dissolved in CHCl$_3$ (50 mL). The organic phase was washed with 5% aq KHSO$_4$ (3×20 mL), brine (1×20 mL), dried (Na$_2$SO$_4$), and the solvent evaporated. The obtained crude product was dissolved in MeCN/H$_2$O (1:3, v/v; 10 mL), lyophilized, and purified by thick-layer chromatography using glass plates from Merck, Darmstadt (type: PLC Silica gel 60 F$_{254}$, 1 mm). Prior to use the plates were developed with MeOH twice. Upon development with CHCl$_3$/MeOH (2:1, v/v containing 1% AcOH) as solvent system, the area containing homogeneous product was scraped from the plate, the product extracted from the collected silica gel with MeOH, and the solvent evaporated. The lipidated inhibitor (NS-629) was obtained upon lyophilization as colorless powder; yield: 2.8 mg (8%); TLC (CHCl$_3$/MeOH/AcOH 13:5:0.18, v/v/v) R$_f$ 0.62; ESI-MS: m/z=1762.0 [M−2H]$^{2-}$; calcd for C$_{167}$H$_{319}$N$_8$O$_{66}$P: 1761.6 (most abundant signal for n=46). The chemical structure of NS-629 for is shown in FIG. 2.

Example 2

Titration of Cathepsin B Active Site with Lipidated Inhibitor NS-629

Powdered lipidated inhibitor of Cathepsin B, NS-629, was dissolved in 0.1 M phosphate buffer, pH 6.0, containing 1 mM EDTA and 0.1% (v/v) PEG for final concentration of 0.05 µM. The kinetic reaction between Cathepsin B and its lipidated inhibitor was analyzed by continuous measurements of the loss of enzymatic activity at different concentration of inhibitor in the presence of fluorogenic substrate Z-Arg-Arg-AMC (AMC=7-amido-4-methylcoumarin) (Bachem). Inhibitor NS-629 in increasing concentrations (0.01-0.06 mM concentration), recombinant Cathepsin B (0.05 mM) and the dithiothreitole (DTT) (0.5 mM) were mixed in a plate with 0.1 M phosphate buffer, pH 6.0, containing 1 mM EDTA and 0.1% (v/v) PEG. After 15 minutes incubation at 37° C. the inhibition kinetics of Cathepsin B and NS-629 were determined. The reaction was started by the addition of 150 µl of Cathepsin substrate Z-Arg-Arg-AMC solution and the kinetics of substrate hydrolysis was monitored continuously during 10 min by a TECAN plate reader at excitation and emission wavelengths of 370 and 460 nm, respectively. As can be seen in FIG. 3a, the inhibitor bound to Cathepsin B with an apparent 1:1.5 stoichiometry, suggesting that Cathepsin B efficiently binds NS-629.

Example 3

Lipid Vesicles Linked with Lipidated Inhibitor Preparation by Extrusion

Aliquots of lipids (2.6 mM of egg phosphatidylcholine (Avanti Polar Lipids, Inc.) and 0.1 mM of lipidated inhibitor) supplied as chloroform solutions are placed into vials to form thin films by removing chloroform by evaporation under vacuum. Dry films are then hydrated by adding of the 0.1 mM phosphate buffer pH 6.0. Dispersions are homogenized with vortex mixing and extruded under pressure through polycarbonate filters of decreasing pore diameter 0.1 µm using extruder. FIG. 4 shows the size distribution of liposomes functionalized with lipidated inhibitor as determined by dynamic light scattering (DLS). The average size was shown to be 85.66 nm.

Example 4

Lipid Vesicles Linked with Lipidated Inhibitor Preparation by Sonification

Aliquots of lipids (2.6 mM of egg phosphatidylcholine (Avanti Polar Lipids, Inc.) and 0.1 mM of lipidated inhibitor) supplied as chloroform solutions are placed into vials to form thin films by removing chloroform by evaporation under vacuum. Dry films are then hydrated by adding of the 0.1 mM phosphate buffer pH 6.0. Dispersions are homogenized with vortex mixing and then emulsified by sonication in bath sonicator during 20 min.

Example 5

Titration of Cathepsin B Active Site with Liposomes Labelled by Lipidated Inhibitor NS-629

The liposomes labelled by lipidated inhibitor were prepared as described above in Example 3. The kinetic reaction between Cathepsin B and liposomes labelled by lipidated Cathepsin inhibitor NS-629 was analyzed by continuous measurements of the loss of enzymatic activity at different concentration of inhibitor in the presence of fluorogenic substrate Z-Arg-Arg-AMC. Liposomes labelled by Cathepsin inhibitor NS-629 in increasing inhibitor concentrations (0.01-0.09 mM concentration) in increasing concentrations (0.01-0.06 mM concentration), recombinant Cathepsin B (0.05 mM) and the DTT (0.5 mM) were mixed in a plate with 0.1 M phosphate buffer, pH 6.0, containing 1 mM EDTA and 0.1% (v/v) PEG. After 15 minutes incubation at 37° C. the inhibition kinetics of Cathepsin B and NS-629 were determined. The reaction was started by the addition of 150 µl of Cathepsin substrate Z-Arg-Arg-AMC solution and the kinetics of substrate hydrolysis was monitored continuously during 10 min by a TECAN plate reader at excitation and emission wavelengths of 370 and 460 nm, respectively. As can be seen in FIG. 3a, the liposomes labelled by Cathepsin inhibitor NS-629 bound to Cathepsin B with an apparent 1:2.5 stoichiometry, suggesting that Cathepsin B could efficiently bind liposomes labelled by Cathepsin inhibitor NS-629.

Example 6

Ex Vivo Binding of Alexa Fluor 555™ (Invitrogen) Loaded Liposomes Labeled by Lipidated Inhibitor to Mouse Bone Marrow-Derived Macrophages Liposomes were prepared as: aliquots of lipids (2.6 mM of egg phosphatidylcholine (Avanti Polar Lipids, Inc.) and 0.1 mM of lipidated inhibitor) supplied as chloroform solutions are placed into vials to form thin films by removing chloroform by evaporation under vacuum. Dry films are then hydrated by adding of 0.1 mg Alexa Fluor 555™ (Invitrogen) containing 0.01 M phosphate buffer, pH 7.4. Active endocytosis of macrophages was stopped by incubation at 4° C. during 15 minutes. Next, 200 µl of liposomes were placed on the cells and incubated for 15 minutes at 4° C. After incubation cells were washed by PBS and fluorescence intensity was examined with TECAN plate reader. FIG. 4 shows that this experiment proves targeting of liposomes with lipidated Cathepsin inhibitor to the immune cells. Liposomes functionalized (NS-Lip-Alx) and not functionalized (Lip-Alx) with NS-629 were loaded with fluorescence marker (Alexa Fluor 555™ (Invitrogen)) and incubated with mouse bone marrow-derived macrophages for 15 minutes at 4° C. Fluorescence of accumulated marker was measured with TECAN plate reader. As a control liposomes without labeling were used.

Example 7

Ex Vivo Binding of Alexa Fluor 555™ (Invitrogen) Loaded Liposomes Labeled by Lipidated Inhibitor to Mouse Bone Marrow-Derived Macrophages Liposomes were prepared as: aliquots of lipids (2.6 mM of egg phosphatidylcholine (Avanti Polar Lipids, Inc.) and 0.1 mM of lipidated inhibitor) supplied as chloroform solutions are placed into vials to form thin films by removing chloroform by evaporation under vacuum. Dry films are then hydrated by adding of 0.1 mg Alexa Fluor 555™ (Invitrogen) containing 0.01 M phosphate buffer, pH 7.4. Active endocytosis of macrophages was stopped by incubation at 4° C. during 15 minutes. Next, 200 µl of liposomes were placed on the cells and incubated for 15 minutes at 4° C. After incubation cells were washed by PBS and examined with an Olympus fluorescent microscope (Olympus IX 81, Olympus) with Imaging Software for Life Science Microscopy Cell. Non-functionalized liposomes (Lip-Alx) and liposomes functionalized with NS-629 (NS-Lip-Alx) were examined with an Olympus fluorescence microscope (Olympus IX 81, Olympus) with Imaging Software for Life Science Microscopy Cell. FIG. 6 shows representation of liposomes with lipidated Cathepsin inhibitor targeting efficiency in primary mouse immune cells.

Example 8

Encapsulation of Magnevist® (Bayer HealthCare Pharmaceuticals) (Dimeglumine Salt of Gd-DTPA; Bayer AG) into the Liposome with Following Extrusion Aliquots of lipids (2.6 mM of egg phosphatidylcholine (Avanti Polar Lipids, Inc.) and 0.1 mM of lipidated inhibitor) supplied as chloroform solutions are placed into vials to form thin films by removing chloroform by evaporation under vacuum. Dry films are then hydrated by adding of Magnevist® (Bayer HealthCare Pharmaceuticals). Dispersions are homogenized with vortex mixing and extruded under pressure through polycarbonate filters of decreasing pore diameter 0.1 µm using extruder. $T_1$-weighted MR images (TE=8.5 ms, TR=400 ms) of an orthotopic transplanted breast cancer mouse before, 1 and 24 hours after ($T_1$) intraperitoneal injection of 200 µl NS-629 labeled liposomes containing Magnevist® (Bayer HealthCare Pharmaceuticals) are shown in FIG. 8. The tumour tissue possess negative MR signal on $T_1$-weighted images. The bright signal at 1 and 24 hours after injection in $T_1$-weighted MR image shows successful targeting of Magnevist® (Bayer HealthCare Pharmaceuticals) loaded NS-629 labelled liposomes.

Example 9

Encapsulation of D-luciferine into the Liposome with Following Extrusion

Aliquots of lipids (2.6 mM of egg phosphatidylcholine (Avanti Polar Lipids, Inc.) and 0.1 mM of lipidated inhibitor) supplied as chloroform solutions are placed into vials to form thin films by removing chloroform by evaporation under vacuum. Dry films are then hydrated by adding of D-luciferine in PBS (15 mg/ml). Dispersions are homogenized with vortex mixing and extruded under pressure through polycarbonate filters of decreasing pore diameter 0.1 µm using extruder. Targeted delivery of liposomes labeled by lipidated inhibitor carrying D-luciferin into transgenic mouse expressing luciferase (FVB.luc$^{rg/+}$) is shown in FIG. 7. The high-intensity luciferase signal associated with the induced paw edema demonstrates selective accumulation of labelled liposomes in the inflammation area.

REFERENCES

Allen, T. M. et al., 1995, Biochim Biophys Acta 1237(2): 99-108.
Altmann et al., 2002, J. Med. Chem. 45: 2352-2354.
Beste et al., 1999, Proc. Natl. Acad. Sci. USA, 96: 1898-1903.
Bieth J. G., 1995, Methods Enzymol., 248: 59-84.
Blume, G. et al., 1993, Biochim Biophys Acta 1149(1): 180-184.
Bromme et al., 1989, Biochem. J. 263: 861-866.
Bromme et al., 1994, Methods Enzymol. 244: 671-685.
Brömme et al., 1996, Biochem. J. 315: 85-89.
Cegnar M. et al., 2004, Experimental Cell Research, 301(2), 223-231.
Chapman H. A. et al., 1997, Annu Rev Physiol, 59: 63-88.
Coussens L. M. et al., 2002, Science; 295: 2387-92.
Cruz et al., 2010, Molecular Pharmaceutics 8: 104-116.
Deaton & Kumar, 2004, Progress in Medicinal Chemistry, 42: 245-375.
Duffy et al., 1999, Bioorg. Med. Chem. Lett. 9: 1907-1910.
Esser R. E. et al., 1994, Arthritis Rheum. 37: 236-47.
Etherington D. J. et al., 1988, Br J Exp Pathol, 69: 281-9.
Fahmy et al., 2007, AAPS Journal 9(2): E171-E180.
Falgueyret et al., 2001, J. Med. Chem. 44: 94-104.
Ferrari, 2005, Nature Reviews 5: 161-171.
Friedrichs, B. et al., 2003, J Clin Invest 111(11): 1733-1745.
Gocheva, V. et al., 2010, Genes Dev 24(3): 241-255.
Greenspan et al., 2001, J. Med. Chem. 44: 4524-4534.
Hansen T. et al., 2000, J Rheumatol, 27: 859-65.
Harmsen & De Haard, 2007, Applied Microbiology and Biotechnology, 77(1), 13-22.

Holliger & Hudson, Nature Biotech., 2005, 23(9): 1126-1136.
Honey, K. et al., 2002, Nat Immunol 3(11): 1069-1074.
Hill P. A. et al., 1994, J Cell Biochem, 56: 118-30.
Huang et al., 2002, J. Med. Chem. 45: 676-684.
Huet G. et al., 1993, Arthritis Rheum, 36: 772-80.
Hylarides et al., 2001, Bioconjugate Chemistry 12, 421-427.
Jaffer Farouc A. et al., 2009, Arterioslerosis Thrombosis and Vascular Biology, 29(7), 1017.
Jane, D. T. et al., 2006, Biol Chem 387(2): 223-234.
Jedeszko C. & Sloane B. F., 2004, Biol Chem, 385: 1017-27.
Joyce J. A. et al., 2004, Cancer Cell, 5:443-53.
Katunuma et al., 1999, FEBS Lett. 458: 6-10.
Katunuma et al., 2000, Biochem. Biophys. Res. Commun. 267: 850-854.
Katunuma et al., 2002, Arch. Biochem. Biophys. 397: 305-311.
Keyszer G. et al., 1998, Arthritis Rheum, 41: 1378-87.
Lechner, A. M. et al., 2006, J Biol Chem 281(51): 39588-39597.
Lemaire R. et al., 1997, Br J Rheumatol, 36: 735-43.
Lenar et al., 1998, Biol Chem Hoppe Seyler, 369 Suppl: 257-61.
Krantz in: A. J. Barrett (Ed.), Methods Enzymol., vol. 244, Academic Press, New York, 1994, pp. 656-671.
Liang et al., 2002, Journal of Controlled Release 78, 67-79.
Link, J. O. et al., 2006, Curr. Opin. Drug Discov. Devel., 9, 471.
Liotta, L. A. & Kohn, E. C., 2001, Nature 411: 375-379.
Mantovani A. et al., 2008, Cancer-related inflammation. Nature 454: 436-444.
Marquis et al., 1998, J. Med. Chem. 41: 3563-3567.
Marquis et al., 1999, Bioorg. Med. Chem. 7: 581-588.
Marquis et al. (1), 2001, J. Med. Chem. 44: 1380-1395.
Marquis et al. (2), 2001, J. Med. Chem. 44: 725-736.
McKerrow et al., 1999, Bioorg. Med. Chem. 7: 639-644.
Mirković B. et al., 2009, FEBS J., 276(17): 4739-51.
Mohamed, M. M. & Sloane, B. F., 2006, Nat Rev Cancer 6(10): 764-775.
Mueller, M. M. & Fusenig, N. E., 2004, Nat. Rev. Cancer 4(11): 839-849.
Murdoch C, et al., 2008, Nat Rev Cancer 8: 618-63.
Orive et al., 2009, Nature Reviews Neuroscience 10: 682-692.
Peer et al., 2007, Nature Nanotechnology 2: 751-760.
Palmer et al., 1995, J. Med. Chem. 38: 3193-3196.
Potts, W. et al., 2004, Int J Exp Pathol 85(2): 85-96.
Quasba et al., 2008, Biotechnology Progress 24 (3), 520-526.
Reinheckel, T. et al., 2005, J Cell Sci 118(Pt 15): 3387-3395.
Robichaud et al., 2003, J. Med. Chem. 46: 3709-3727.
Rossi, A. et al., A., 2004, Biol Chem 385(5): 363-372.
Rossin et al., 2005, The Journal of Nuclear Medicine 46: 1210-1218.
Roth, W. et al., 2000, FASEB J 14(13): 2075-2086.
Saegusa et al., 2002, J. Clin. Invest. 110: 361-369.
Schaschke et al., 1996, FEBS Lett., 391: 297-301.
Schaschke et al., 1998, J. Am. Chem. Soc., 1998: 7030-7038.
Schaschke et al. (1), 2000, FEBS Lett. 482: 91.
Schaschke et al. (2), 2000, Bioorganic & Medicinal Chemistry Letters, 10: 677-680.
Schedel J. et al., 2004, Gene Ther, 11: 1040-7.
Seyfried et al., 2001, Brain Res. 901: 94-101.
Shaw, 1994, Methods Enzymol. 244: 649-656.
Shuvaev et al., 2004, Methods in Molecular Biology 283: 3-19.
Skerra (1), 2000, Biochim. Biophys. Acta, 1482: 337-50.
Skerra (2), 2000, J. Mol. Recognit., 13: 167-187.
Smith et al., 2001, Bioorg. Med. Chem. Lett., 11: 2951-2954.
Sun et al., 2008, Advanced Drug Delivery Reviews 60, 1252-1265.
Tavares et al. (1), 2004, J. Med. Chem. 47: 588-599.
Tavares et al. (2), 2004, J. Med. Chem. 47: 5049-5056.
Tavares et al. (3), 2004, J. Med. Chem. 47: 5057-5068.
Thompson et al., 1997, Proc. Natl. Acad. Sci. U.S.A. 94: 14249-14254.
Thompson et al., 1998, J. Med. Chem. 41: 3923-3927.
Thurmond et al. (1), 2004, Pharmacol. Exp. Ther., 308: 268.
Thurmond et al. (2), 2004, J. Pharmacol. Exp. Ther. 308: 268-276.
Thurmond et al. (3), 2004, J. Med. Chem. 47: 4799-4801.
Turk, B. et al., 2000, Biochim Biophys Acta 1477(1-2): 98-111.
Turk V., et al., 2004, Cancer Cell, 5: 409-10.
Vasiljeva, O. et al., 2006, Cancer Res 66(10): 5242-5250.
Vasiljeva, O. et al., 2007, Current Pharmaceutical Design 13: 385-401.
Vasiljeva, O. et al., Curr. Pharm. Des., 2007, 13: 387
Ward et al., 2002, J. Med. Chem. 45: 5471-5482.
Wolters, P. J. et al., 2001, J Biol Chem 276(21): 18551-18556.
Yasuda et al., 2005, Advanced Drug Delivery Reviews, 57: 973-993.
Yasuma et al., 1998, J. Med. Chem. 41: 4301-4308.
Zhou et al., 2001, Arkivoc VI, 116-121.
Zhou et al., 2002, Bioorg. Med. Chem. Lett. 12: 3417-3419.
Zhou et al., 2003, Bioorg. Med. Chem. Lett. 12: 139-141.

The invention claimed is:

1. A Cathepsin binding and liposome-binding compound having the structure of formula (XIII):

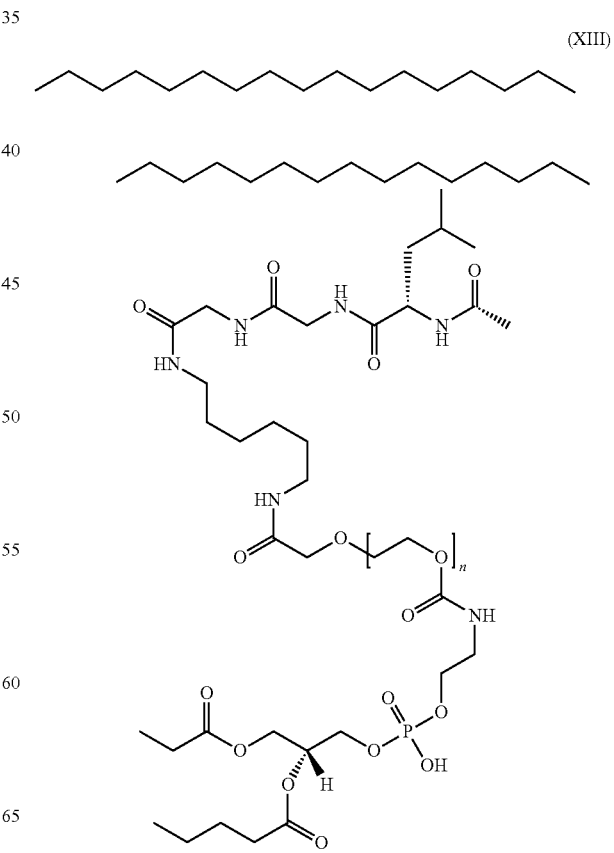

(XIII)

-continued
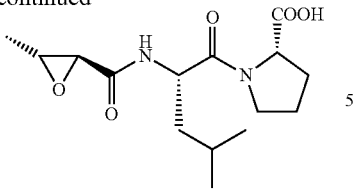
wherein n=38 to 53.
2. A Cathepsin targeting compound, comprising the Cathepsin binding and liposome-binding compound of claim 1, bound to a liposome.
3. The Cathepsin targeting compound according to claim 2, comprising a diagnostic moiety.
* * * * *

UNITED STATES PATENT AND TRADEMARK OFFICE
CERTIFICATE OF CORRECTION

PATENT NO. : 9,827,337 B2
APPLICATION NO. : 14/127758
DATED : November 28, 2017
INVENTOR(S) : Olga Vasiljeva et al.

Page 1 of 1

It is certified that error appears in the above-identified patent and that said Letters Patent is hereby corrected as shown below:

Columns 30-31, in Claim 1, should read:

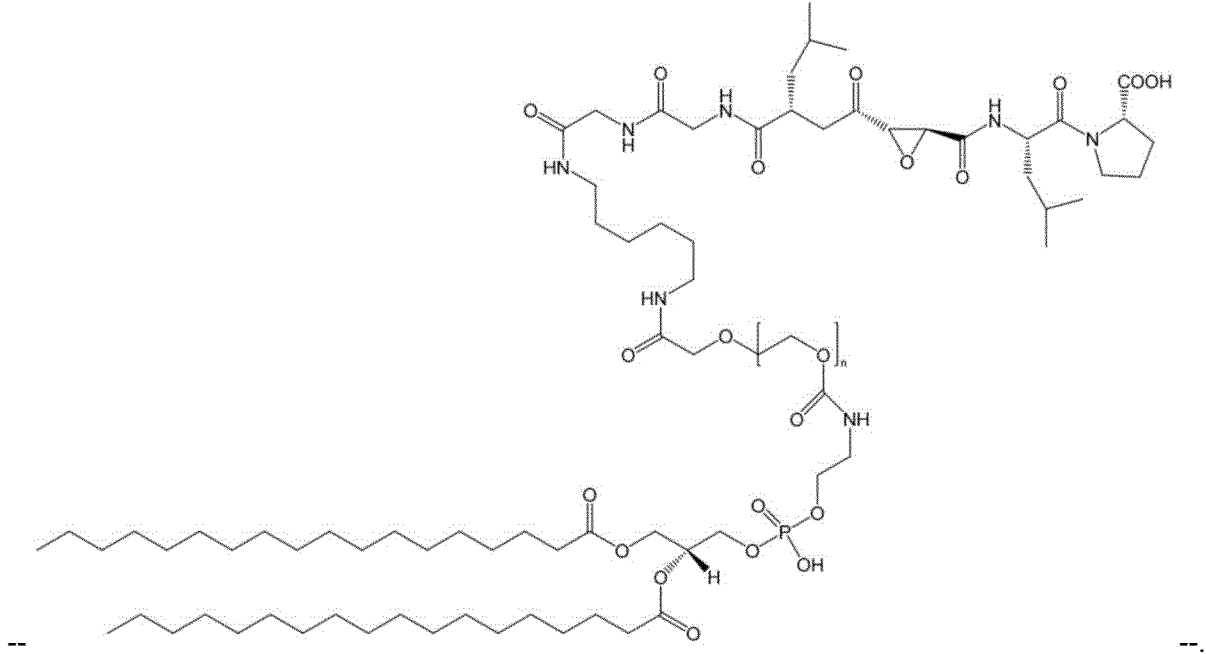

Signed and Sealed this
Thirteenth Day of November, 2018

Andrei Iancu
*Director of the United States Patent and Trademark Office*